US005863753A

United States Patent [19]
Haugland et al.

[11] Patent Number: 5,863,753
[45] Date of Patent: *Jan. 26, 1999

[54] CHEMICALLY REACTIVE UNSYMMETRICAL CYANINE DYES AND THEIR CONJUGATES

[75] Inventors: Richard P. Haugland; Victoria L. Singer; Stephen T. Yue; Paul J. Millard, all of Eugene, Oreg.

[73] Assignee: Molecular Probes, Inc., Eugene, Oreg.

[*] Notice: The term of this patent shall not extend beyond the expiration date of Pat. No. 5,658,751.

[21] Appl. No.: 914,439

[22] Filed: Aug. 19, 1997

Related U.S. Application Data

[63] Continuation-in-part of Ser. No. 331,031, Oct. 27, 1994, Pat. No. 5,658,751.

[51] Int. Cl.$^6$ .............................. C12Q 1/04; C12Q 1/00; C12Q 1/02
[52] U.S. Cl. ................................. 435/34; 435/4; 435/29; 435/6; 436/94; 436/800; 536/1.11; 536/26.73; 536/25.6
[58] Field of Search .................................. 435/34, 4, 29, 435/6; 436/94, 800; 536/1.11, 26.73, 25.6

[56] References Cited

U.S. PATENT DOCUMENTS

| | | | |
|---|---|---|---|
| 4,711,955 | 12/1987 | Ward et al. | 435/34 |
| 4,737,454 | 4/1988 | Dattagupta et al. | 435/34 |
| 4,883,867 | 11/1989 | Lee et al. | 435/34 |
| 4,921,805 | 5/1990 | Gebeyehu et al. | 435/34 |
| 4,937,198 | 6/1990 | Lee et al. | 435/34 |
| 4,997,928 | 3/1991 | Hobbs, Jr. | 435/34 |
| 5,047,519 | 9/1991 | Hobbs, Jr. et al. | 435/34 |
| 5,171,534 | 12/1992 | Smith et al. | 435/34 |
| 5,321,130 | 6/1994 | Yue et al. | 435/34 |
| 5,332,666 | 7/1994 | Prober et al. | 435/34 |
| 5,436,134 | 7/1995 | Haugland et al. | 435/34 |
| 5,445,946 | 8/1995 | Roth et al. | 435/34 |
| 5,534,416 | 7/1996 | Millard et al. | 435/34 |
| 5,545,535 | 8/1996 | Roth et al. | 435/34 |
| 5,582,977 | 12/1996 | Yue et al. | 435/34 |
| 5,597,696 | 1/1997 | Linn et al. | 435/34 |
| 5,658,751 | 8/1997 | Yue et al. | 435/34 |

FOREIGN PATENT DOCUMENTS

| | | |
|---|---|---|
| 0 492 570 A1 | 7/1992 | European Pat. Off. . |
| 0 710 668 A2 | 5/1996 | European Pat. Off. . |
| 0 714 986 A1 | 6/1996 | European Pat. Off. . |
| 1529202 | 1/1978 | United Kingdom . |
| WO 94/05688 | 3/1994 | WIPO . |
| WO 97/45539 | 5/1997 | WIPO . |

OTHER PUBLICATIONS

Brinkley, Bioconjugate Chem., 3,2 (1992).
R. Haugland, Molecular Probes Handbook of Fluorescent Probes and Research Chemicals, Chapters 1–3, (1996).
Dean et al., Affinity Chromatography, A Practical Approach, IRL Press, 1985 pp. 34–35.
Ishiguro et al., Nucleic Acids Research 24, 4992 (1996).
Bolton et al. Nucleic Acids Research 5, 4891 (1978).

*Primary Examiner*—Louise N. Leary
*Attorney, Agent, or Firm*—Allegra J. Helfenstein; Anton E. Skaugset

[57] ABSTRACT

The invention comprises cyanine dyes, in particular chemically reactive dyes, conjugates of reactive cyanine dyes, the non-covalent complexes of nucleic acids with the dyes and dye-conjugates of the invention, and a method of forming a nucleic acid complex with the dyes and dye-conjugates of the present invention. The dyes of the invention are useful for the preparation of dye-conjugates. The presence of a reactive group on the unsymmetrical cyanine dyes of the invention facilitates their covalent conjugation to a variety of substances, both biological and synthetic.

70 Claims, 2 Drawing Sheets

CHEMICALLY REACTIVE UNSYMMETRICAL CYANINE DYES AND THEIR CONJUGATES

This application is a continuation-in-part of application Ser. No. 08/331,031, filed Oct. 27, 1994, now U.S. Pat. No. 5,658,751.

FIELD OF THE INVENTION

The invention relates to unsymmetrical cyanine dyes that are fluorescent stains for nucleic acids, that additionally possess a chemically reactive functional group. The reactive dyes of the invention are useful for the preparation of dye-conjugates that non-covalently bind nucleic acids.

BACKGROUND

A variety of unsymmetrical cyanine dyes and derivatives thereof have been shown to be effective fluorescent stains for nucleic acids. Selected properties of such dyes, such as the brightness, spectral properties, detectability, photostability, affinity for nucleic acids, or selectivity for ss DNA, ds DNA or RNA vary with type and location of dye substituents. Some cyanine dyes are effective stains for reticulocyte analysis (U.S. Pat. No. 4,883,867 to Lee, et al. (1989)) and for bloodborne parasites (U.S. Pat. No. 4,937,198 to Lee, et al. (1990)). Other substituted cyanine dyes are typically more fluorescent than the cyanine dyes of Lee et al., and are capable of permeating a variety of cells and electrophoretic gels (U.S. Pat. No. 5,436,134 to Haugland, et al. (1995); U.S. Pat. No. 5,545,535 to Roth et al. (1996); U.S. Pat. No. 5,534,416 to Millard, et al. (1996); and U.S. Pat. No. 5,445,946 to Roth et al. (1995), all incorporated by reference).

Substitution of a cationic side chain makes selected cyanine dyes relatively impermeant to cell membranes (U.S. Pat. No. 5,321,130 to Yue et al. (1994), incorporated by reference), while the substitution of heteroatom-containing side chains also substantially modifies the permeability, selectivity and affinity of the dye for nucleic acids (SUBSTITUTED UNSYMMETRICAL CYANINE DYES WITH SELECTED PERMEABILITY, Ser. No. 08/331,031 by Yue et al., filed Oct. 27, 1994, incorporated by reference).

Chemically reactive compounds have typically been utilized to impart the physical or spectral properties of the compound onto a selected substrate, as in the fluorescent labeling of proteins. Nucleic acid capture reagents comprising methidium have been covalently attached to solid supports, producing materials that bind and subsequently release nucleic acids (U.S. Pat. No. 4,921,805 to Gebeyehu et al. (1990)). Similarly, the attachment of a reactive ester of a carboxylic acid to selected cyanine dyes allows them to be tethered to oligonucleotides, and thereby detect the binding of a target oligonucleotide (U.S. Pat. No. 5,597,696 to Linn et al. (1997)).

The present invention describes chemically reactive versions of cyanine dyes. The invention also describes conjugates of the cyanine dyes prepared using the chemically reactive dyes, and the complex of the dyes of the invention with nucleic acids. Cyanine dyes that are photoreactive possess substantial utility for controlled labeling of biological materials, including nucleic acids. The dye-conjugates of the invention possess utility for the analysis of interactions between proteins and other substrates with nucleic acids, or for immobilizing nucleic acids.

SUMMARY OF THE INVENTION AND DESCRIPTION OF PREFERRED EMBODIMENTS

Figure 1:
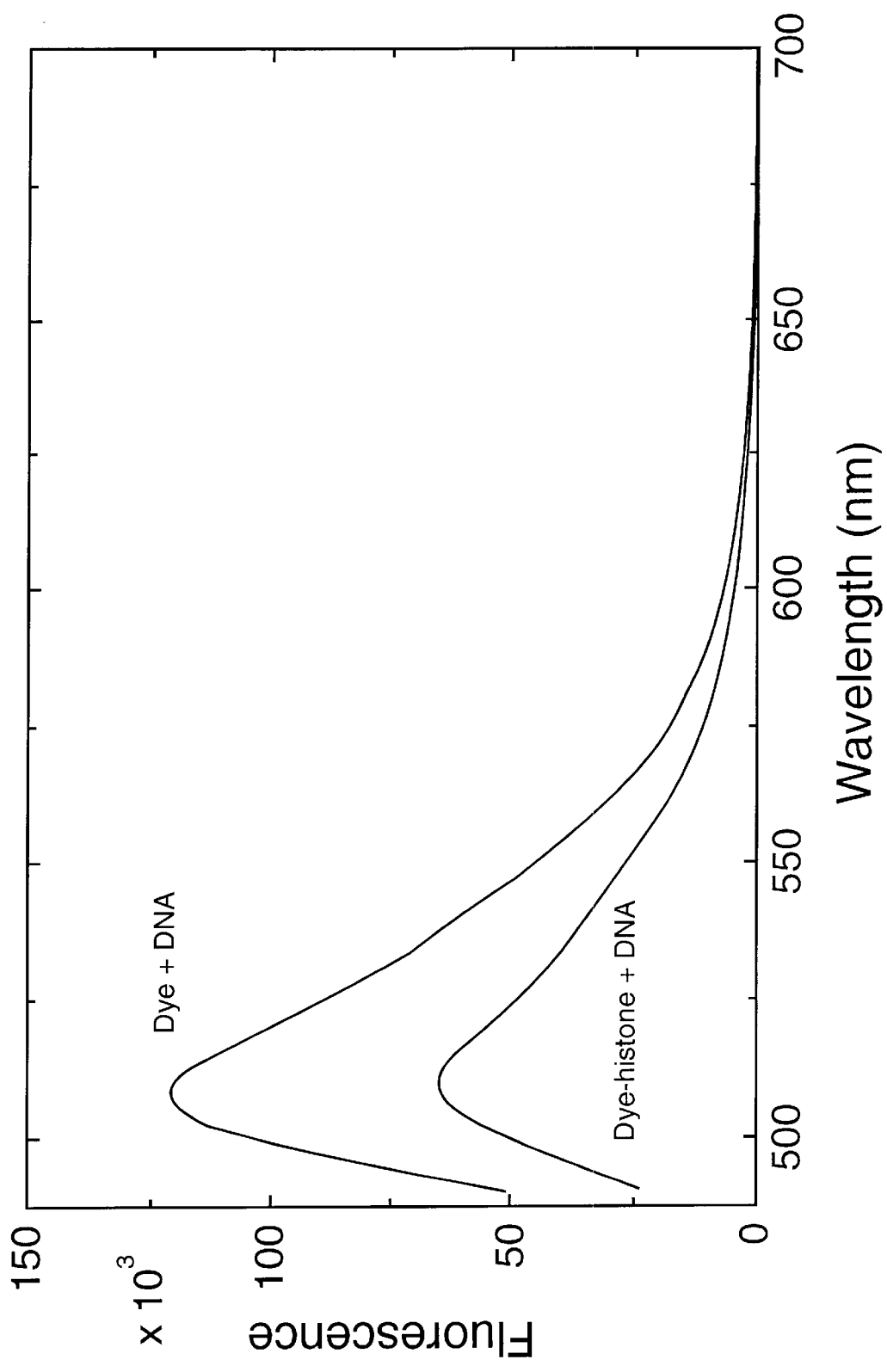
FIG. 1: Photoaffinity labeling of DNA using a photoreactive compound of the invention, as described in Example 27.

The presence of a reactive group on the unsymmetrical cyanine dyes of the invention facilitates their covalent conjugation to a variety of substances, both biological and synthetic. The dyes and dye-conjugates of the invention exhibit a fluorescence enhancement upon binding non-covalently to nucleic acids. The invention comprises cyanine dyes, in particular chemically reactive dyes, conjugates of reactive cyanine dyes, the non-covalent complexes of nucleic acids with the dyes and dye-conjugates of the invention, and a method of forming a nucleic acid complex with the dyes and dye-conjugates of the present invention.

Dye Structure

The dyes of the invention comprise: 1) a first heterocyclic ring system that is a substituted benzazolium ring, 2) a bridging methine and 3) a second heterocyclic ring that is a pyridinium or quinolinium ring system. In one aspect of the invention, one or more positions of which are substituted by a chemically reactive functional group, or a conjugated substance. In another aspect of the invention, the position adjacent to the pyridinium or quinolinium nitrogen is substituted by an aryl or heteroaryl moiety. The dyes of the invention are optionally substituted by a TAIL moiety that contains at least one heteroatom, or by a cyclic substituent. The first and second ring systems are optionally further substituted by a variety of substituents, as described below.

Core Structure

The core structure of the dyes of the present invention are described by the formula:

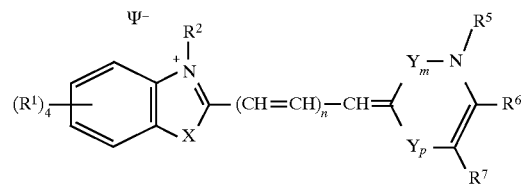

where the substituted benzazolium ring system on the left is linked by a methine bridge to the right-hand pyridinium or quinolinium ring system. One or more substituents on the core structure is a reactive functional group, or a conjugated substance.

Although each $R^1$ on the benzazolium ring system is typically H, incorporation of one or more non-hydrogen substituents $R^1$ can be used to fine tune the absorption and emission spectrum of the resulting dye. The benzazole may contain more than one nonhydrogen substituent $R^1$, which may be the same or different. Where any $R^1$ is not hydrogen, it is optionally an alkyl group having from 1–6 carbons; or a trifluoromethyl; or a halogen; or an alkoxy having 1–6 carbons. Each $R^1$ is optionally a covalently bound reactive moiety, -L-$R_x$, or a covalently bound conjugated substance, -L-$S_c$. Typically, each compound contains no more than one $R^1$ that is not hydrogen. Preferably, each $R^1$ is H or alkoxy, more preferably each $R^1$ is H.

The substituent $R^2$ is an alkyl group having 1–6 carbons, preferably methyl or ethyl, more preferably methyl. Alternatively, $R^2$ is a covalently bound reactive moiety -L-$R_x$, or a covalently bound conjugated substance, -L-$S_c$.

The counterion ψ⁻ is a biologically compatible ion, as described above. Preferred ψ⁻ counterions are chloride, iodide, perchlorate, or various sulfonates.

X is one of O, S, Se or $NR^{15}$, where $R^{15}$ is an alkyl group having 1–6 carbons. Alternatively, X is $CR^{16}R^{17}$, where $R^{16}$ and $R^{17}$, which may be the same or different, are independently H or alkyl groups having 1–6 carbons, or the carbons of $R^{16}$ and $R^{17}$ taken in combination complete a five or six membered saturated ring. When X is $CR^{16}R^{17}$, $R^{16}$ and $R^{17}$ are typically methyls. Preferably, X is O or S.

The two heterocyclic ring systems are linked by 1, 3 or 5 methine (—CH=) groups in such a way as to permit extensive electronic delocalization. The number of methine groups between the heteroaromatic rings influences the spectral properties of the dye. Preferably n=0 or 1, more preferably n=0.

The N-bound substituent $R^5$ is an alkyl group having 1–6 carbons that is saturated or unsaturated, linear or branched. Alternatively, $R^5$ is a cyclic substituent, or $R^5$ is a TAIL. Typically $R^5$ is an alkyl having 1–6 carbons, preferably 1–2 carbons, or $R^5$ is a cyclic substituent. Alternatively, $R^5$ is a TAIL, -L-$R_x$ or -L-$S_c$. In one aspect of the invention, when $R^5$ is a TAIL, the SPACER moiety incorporates a phenylene linkage.

When $R^5$ is a cyclic substituent, $R^5$ is typically an aryl, heteroaryl, or cycloalkyl having 3–10 carbons. Typically the aryl is a phenyl or naphthyl group, and the heteroaryl substituent is a 5- or 6-membered heteroaromatic ring, wherein the heteroatom is O, N or S. Examples of alicyclic and heteroalicyclic substitutents are substituted or unsubstituted cyclohexyls, cyclohexenyls, morpholinos, piperidinyls and piperazinyls. Examples of aromatic and heteroaromatic cyclic substituents include substituted or unsubstituted naphthyls, phenyls, thienyls, benzothiazolyls, furanyls, oxazolyls, benzoxazolyls, and pyridinyls. Substituents on such cyclic substituents are independently hydrogen, halogen, alkyl, perfluoroalkyl, amino, alkylamino, dialkylamino, alkoxy or carboxyalkyl, each alkyl group having 1–6 carbons. Preferred cyclic substituents are substituted or unsubstituted naphthyl, phenyl, thienyl, morpholino, and cycloalkyl having 3–10 carbons, more preferably substituted or unsubstituted phenyl.

The second ring system contains a ring fragment Y that is —$CR^3$=$CR^4$—, with subscripts p and m equal to 0 or 1, such that p+m=1. For all embodiments, the ring contains a 6 membered pyridinium-based heterocycle according to one of these formulations

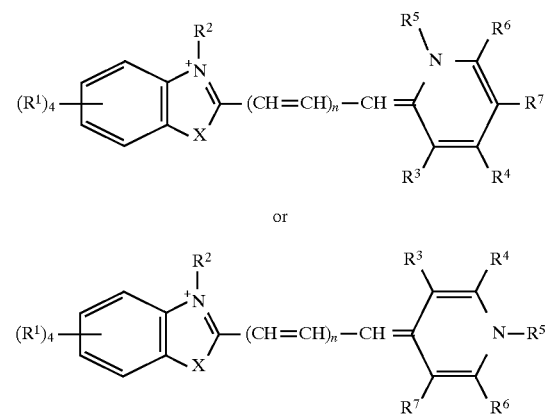

or

In preferred embodiments of the invention, m=1 and p=0 ("4-pyridiniums" and "4-quinoliniums").

The ring substituent $R^4$ is H, or a halogen, or an alkyl having 1–6 carbons that is saturated or unsaturated, linear or branched. $R^4$ is optionally a cyclic substituent, as described above, or —$OR^8$, —$SR^8$, or —($NR^8R^9$), where $R^8$ and $R^9$, which can be the same or different, are independently alkyl groups having 1–6 carbons, 1–2 alicyclic or aromatic rings, or $R^8$ and $R^9$ taken in combination are —(CH$_2$)$_2$—V—(CH$_2$)$_2$— where V is a single bond, —O—, —CH$_2$—, or —$NR^{10}$—, where $R^{10}$ is H or an alkyl having 1–6 carbons. Alternatively, $R^4$ is a TAIL, -L-$R_x$, or -L-$S_c$. Preferably, $R^4$ is not hydrogen. In one embodiment of the invention $R^4$ is —$OR^8$, —$SR^8$, or —($NR^8R^9$). In another embodiment of the invention $R^4$ is an alkyl having 1–6 carbons. In yet another embodiment of the invention, $R^4$ is a TAIL.

In one aspect of the invention, $R^4$ is an aryl or heteroaryl. In one embodiment, $R^4$ is an aryl or heteroaryl that is optionally substituted by halogen, alkyl, perfluoroalkyl, amino, alkylamino, dialkylamino, alkoxy or carboxyalkyl, the alkyl groups of which have 1–6 carbons. In another embodiment, $R^4$ is an aryl or heteroaryl that is substituted by a TAIL, or -L-$R_x$, or -L-$S_c$. Those compounds of the invention wherein $R^4$ is aryl or heteroaryl possessed enhanced photostability when complexed to nucleic acids relative to analogous compounds wherein $R^4$ is not aryl or heteroaryl.

The ring substituents $R^3$, $R^6$, and $R^7$, are independently H, or an alkyl having 1–6 carbons that is saturated or unsaturated, linear or branched. In another embodiment, $R^6$ and $R^7$, taken in combination form a fused 6-membered aromatic ring.

Where $R^6$ and $R^7$ taken in combination form a fused 6-membered aromatic ring, embodiments of this invention are quinolinium derivatives according to the formula

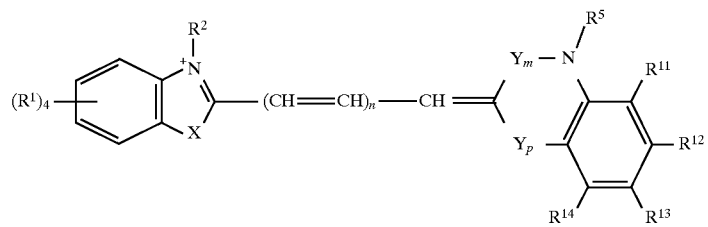

where ring substituents $R^{11}$, $R^{12}$, $R^{13}$, and $R^{14}$ are independently H; or an alkyl having 1–6 carbons that is saturated or unsaturated, linear or branched, or —$OR^8$, —$SR^8$, or —($NR^8R^9$), as defined previously, a TAIL moiety, -L-$R_x$, or -L-$S_c$. Preferred embodiments of the invention are quinoliniums wherein m=1 and p=0 ("4-quinoliniums").

For all embodiments of the invention, at least one of $R^1$, $R^2$, $R^3$, $R^4$, $R^5$, $R^6$, $R^7$, $R^{11}$, $R^{12}$, $R^{13}$, and $R^{14}$ is -L-$R_x$ or -L-$S_c$. Preferably only one of $R^1$, $R^2$, $R^3$, $R^4$, $R^5$, $R^6$, $R^7$, $R^{11}$, $R^{12}$, $R^{13}$, and $R^{14}$ is -L-$R_x$ or -L-$S_c$, however where more than one of $R^1$ $R^2$, $R^3$, $R^4$, $R^5$, $R^6$, $R^7$, $R^{11}$, $R^{12}$, $R^{13}$, and $R^{14}$ is -L-$R_x$ or -L-$S_c$, each -L-$R_x$ and -L-$S_c$ is the same or different.

Additionally, for all embodiments of the invention where m=1 (4-pyridiniums and quinoliniums) and $R^5$ is -L-$R_x$ or -L-$S_c$, $R^4$ is required to be non-hydrogen. Typically dyes where $R^4$ is not hydrogen possess enhanced quantum yields relative to similar dyes wherein $R^4$ is H.

In one embodiment of the invention one or more of $R^3$, $R^4$, $R^5$, $R^6$, $R^7$, $R^{11}$, $R^{12}$, $R^{13}$ and $R^{14}$ is a TAIL. In this embodiment, preferably at least one of $R^4$, $R^6$, or $R^{12}$ is TAIL, more preferably, $R^4$ is a TAIL. When $R^4$ is a TAIL, LINK is preferably —$NR^{20}$— or —S—. When TAIL is at any position other than $R^4$ or $R^5$, LINK is preferably —O— or a single bond.

In another embodiment of the invention, $R^5$ is a cyclic substituent, and $R^4$ is not hydrogen. In this embodiment, preferably $R^4$ is -L-$R_x$ or -L-$S_c$. In yet another embodiment of the invention, $R^5$ is alkyl having 1–6 carbons, and $R^4$ is not hydrogen, preferably -L-$R_x$ or -L-$S_c$. In a specific embodiment of the invention, the dyes of the invention are 4-pyridiniums or 4-quinoliniums, wherein $R^5$ is an alkyl having 1–6 carbons, and $R^4$ is not hydrogen.

Dyes of the present invention that possess a TAIL moiety can be selected to possess particular properties for staining nucleic acids, for example cell permeability and affinity for binding to nucleic acids. However, the selection of an appropriate chemically reactive moiety ($R_x$) or conjugated substance ($S_c$) typically has a profound effect on such properties as well.

In another embodiment of the invention, the cyanine dyes of the invention have the formula

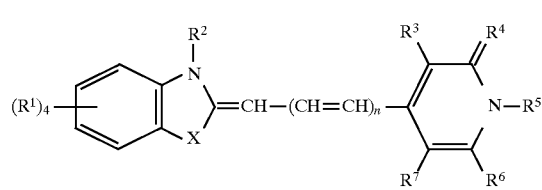

or the formula

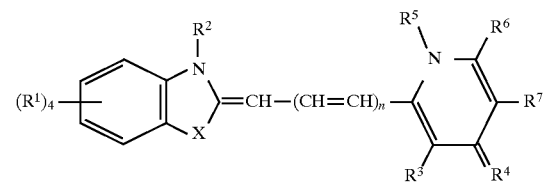

wherein $R^1$, $R^2$, X and n are as defined previously.

In this embodiment, $R^5$ is an alkyl that is saturated or unsaturated, linear or branched, having 1–6 carbons; or $R^5$ is a cyclic substituent that is an aryl or heteroaryl; or a cycloalkyl; or $R^5$ is a TAIL; or $R^5$ is -L-$R_x$. Preferably, $R^5$ is aryl or heteroaryl, more preferably phenyl. $R^4$ is an imine moiety $NR^{19}$; where $R^{19}$ is an alkyl group having 1–6 carbons; or an alicyclic or aromatic ring; or $R^{19}$ is -SPACER-CAP. $R^3$, $R^6$ and $R^7$ are independently H; or an alkyl that is saturated or unsaturated, linear or branched, having 1–6 carbons; or -L-$R_x$.

Alternatively, $R^6$ and $R^7$ form a fused aromatic ring such that said compound has the formula

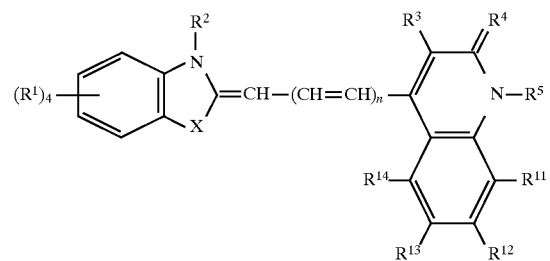

or the formula

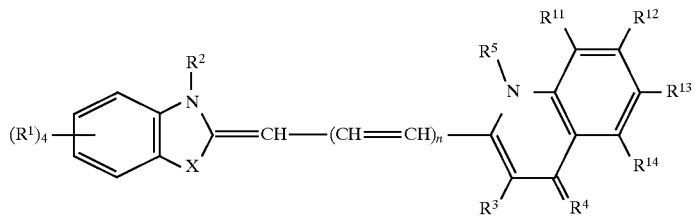

where $R^{11}$, $R^{12}$, $R^{13}$, and $R^{14}$, which may be the same or different, are independently H; or a TAIL or -L-$R_x$; or an alkyl that is saturated or unsaturated, linear or branched, having 1–6 carbons; or —$OR^8$, —$SR^8$, or —($NR^8R^9$), where $R^8$ and $R^9$ are as defined previously. Preferably, $R^6$ and $R^7$ are H; or taken in combination, form a fused aromatic ring. TAIL TAIL is a heteroatom-containing side chain, which is described by the formula LINK-SPACER-CAP. LINK is the linking moiety by which TAIL is attached to the core structure of the dyes of the present invention. SPACER is a covalent linkage that connects LINK to CAP. CAP is the portion of TAIL that possesses a heteroatom component.

LINK is a single covalent bond, an ether linkage (—O—), a thioether linkage (—S—), or an amine linkage (—$NR^{20}$—). In each embodiment, LINK forms the attachment between the dye core structure and SPACER. When LINK is an amine, the amine substituent ($R^{20}$) is optionally H, such that LINK=—NH—. Alternatively, $R^{20}$ is a linear or branched alkyl having 1–8 carbons. In another embodiment of the invention, $R^{20}$ is -SPACER'-CAP', yielding a TAIL having the formula

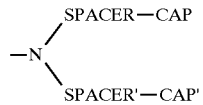

where SPACER' and CAP', respectively, may be the same as or different from SPACER and CAP, and are selected from the same alternatives defined for SPACER and CAP, respectively. For the sake of simplifying the description, SPACER and CAP are defined with the understanding that a description of SPACER includes SPACER', and a description of CAP includes CAP'.

SPACER is a covalent linkage that joins LINK and CAP. SPACER is a linear, branched, cyclic, heterocyclic, saturated or unsaturated arrangement of 1–16 C, N, P, O or S atoms. Alternatively, SPACER is a single covalent bond, such that both LINK and SPACER are not simultaneously single covalent bonds. Preferably, the SPACER linkage must begin and end with a carbon atom. Typically, if SPACER consists of a single atom, it is required to be a carbon atom, so that the first and last atom in SPACER (in this specific instance, they are the same atom) is a carbon. The 1–16 atoms making up SPACER are combined using any appropriate combination of ether, thioether, amine, ester, or amide bonds; or single, double, triple or aromatic carbon—carbon bonds; or phosphorus-oxygen bonds; or phosphorus-sulfur bonds; or nitrogen—nitrogen bonds; or nitrogen-oxygen bonds; or aromatic or heteroaromatic bonds. SPACER is further substituted by hydrogen to accommodate the valence state of each atom in SPACER.

Generally, the atoms of SPACER are arranged such that all heteroatoms in the linear backbone of SPACER are separated by at least one carbon atom, and preferably separated by at least two carbon atoms. Typically, SPACER is 1–6 carbon atoms in a linear or branched saturated chain. In one embodiment of the invention, SPACER incorporates a 6-membered aromatic ring (phenylene linkage). In another embodiment of the invention, SPACER incorporates a 5- or 6-membered heteroaromatic ring, wherein the heteroatoms are O, N, or S. Alternatively, SPACER incorporates amide linkages, ester linkages, simple ethers and thioethers, and amines in a linear arrangement, such as —CH$_2$—CH$_2$—(C=O)—NH—CH$_2$—CH$_2$—CH$_2$—. Preferably, SPACER is a linear chain composed of sequential methylene groups (—(CH$_2$)$_k$—, where k=1–8).

LINK and SPACER, in combination, serve to attach a heteroatom-containing group, CAP, to the dye core structure. CAP may contain oxygen, sulfur or nitrogen, according to the formulas —O—$R^{21}$, —S—$R^{21}$, —NR$^{21}$R$^{22}$, or —N$^+$R$^{21}$R$^{22}$R$^{23}$ ψ$^-$. The substituents $R^{21}$, $R^{22}$, and $R^{23}$ are independently H, or a linear or branched alkyl or cycloalkyl having 1–8 carbons. Where any of $R^{21}$, $R^{22}$ and $R^{23}$ are alkyl or cycloalkyl, they are optionally further substituted by halogen, hydroxy, alkoxy having 1–8 carbons, amino, carboxy, or phenyl, where phenyl is optionally further substituted by halogen, hydroxy, alkoxy having 1–8 carbons, amino, aminoalkyl having 1–8 carbons, or carboxyalkyl having 1–8 carbons. In another embodiment of the invention, one or more of $R^{21}$, $R^{22}$ and $R^{23}$, taken in combination with SPACER forms a 5- or 6-membered ring that is aromatic, heteroaromatic, alicyclic or heteroalicyclic ring. When the 5- or 6-membered ring is heteroaromatic or heteroalicyclic, the ring contains 1–3 heteroatoms that are O, N or S. Alternatively, one or more of $R^{21}$, $R^{22}$, and $R^{23}$, taken in combination with $R^{20}$ and SPACER, forms a 5- or 6-membered ring that is aromatic, heteroaromatic, alicyclic or heteroalicyclic ring, as described above. Preferably, $R^{21}$, $R^{22}$ are hydrogen, or alkyls having 1–8 carbons. $R^{23}$ is typically H or alkyl having 1–8 carbons. When CAP is —N$^+$R$^{21}$R$^{22}$R$^{23}$ ψ$^-$, the substituents $R^{21}$, $R^{22}$ and $R^{23}$ are typically not hydrogen, so that the positive charge present on the ammonium nitrogen is not subject to equilibrium neutralization in aqueous solutions.

When CAP is —N$^+$R$^{21}$R$^{22}$R$^{23}$ ψ$^-$, the biologically compatible counterion ψ$^-$ balances the positive charge present on the CAP nitrogen, which is a quaternary ammonium salt. As used herein, a substance that is biologically compatible is not toxic as used, and does not have a substantially deleterious effect on biomolecules. Examples of ψ$^-$ include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred ψ$^-$ counterions are chloride, iodide, perchlorate and various sulfonates.

Additionally, there are several embodiments of the present invention wherein CAP incorporates a cyclic structure. In these embodiments, CAP typically incorporates a 4- to 10-membered ring, preferably a 5- or 6-membered ring, that contains at least one nitrogen atom. The nitrogen atom incorporated within the cyclic structure is optionally substituted by $R^{23}$ to give an ammonium salt. Where CAP incorporates a cyclic structure, the cyclic structure optionally including an additional heteroatom (typically oxygen or sulfur). Specific versions of CAP include, but are not limited to, those listed in Table 1.

TABLE 1

Examples of specific CAP moieties

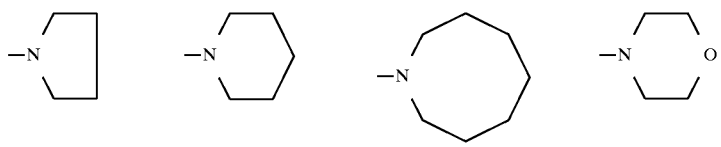

TABLE 1-continued

Examples of specific CAP moieties

[Chemical structures showing various CAP moieties including: —N with S-containing ring; —N with N-containing ring; —N with piperazine-type ring with +N(R21)(R22) ψ−; —N+(R23) ψ−; R23—N+ with O-containing ring ψ−; R23—N+ with ring ψ−; R23—N+ with piperazine with +N(R21)(R22) ψ−; —N+ with pyridinium-type ring ψ−]

CAP is preferably —NR²¹R²² or —N⁺R²¹R²²R²³ ψ⁻, where R²¹, R²², and R²³ are alkyls having 1–6 carbons. More preferably CAP is —N(CH₃)₂ or —N⁺(CH₃)₃ ψ⁻.

Preferably TAIL contains 6–10 non-hydrogen atoms, including LINK and CAP.

Conjugates of Reactive Cyanine Dyes

The reactive dyes of the invention possess at least one group -L-R$_x$, where R$_x$ is the reactive group that is attached to the dye by a covalent linkage L. In certain embodiments R$_x$ is attached to the dye by multiple intervening atoms that serve as a spacer. The dyes with a reactive group (R$_x$) label a wide variety of organic or inorganic substances that contain or are modified to contain functional groups with suitable reactivity, resulting in chemical attachment of the conjugated substance (S$_c$), represented by -L-S$_c$. This conjugation typically confers the nucleic acid-sensing abilities of the cyanine dye on the conjugated substance. The reactive group and functional group are typically an electrophile and a nucleophile that can generate a covalent linkage. Alternatively, the reactive group is a photoactivatable group, and becomes chemically reactive only after illumination with light of an appropriate wavelength. Selected examples of functional groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |

TABLE 2-continued

Examples of some routes to useful covalent linkages

| Electrophilic Group | Nucleophilic Group | Resulting Covalent Linkage |
|---|---|---|
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amineslanilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula -COΩ, where Ω is a good leaving group (e.g. oxysuccinimidyl (—OC₄H₄O₂) oxysulfosuccinimidyl (—OC₄H₃O₂—SO₃H), -1-oxybenzotriazoiyl (—OC₆H₄N₃); or an aryloxy group or aryloxy substituted one or more times by electron withdrawing substituents such as nitro, fluoro, chloro, cyano, or trifluoromethyl, or combinations thereof, used to form an anhydride or mixed anhydride —OCORᵃ or —OCNRᵃNHRᵇ, where Rᵃ and Rᵇ, which may be the same or different, are C₁–C₆ alkyl, C₁–C₆ perfluoroalkyl, or C₁–C₆ alkoxy; or cyclohexyl, 3-dimethylaminopropyl, or N-morpholinoethyl).
**Acyl azides can also rearrange to isocyanates The covalent linkage L binds the reactive group R$_x$ or conjugated substance S$_c$ to the dye, either directly (L is a single bond) or with a combination of stable chemical bonds, optionally including single, double, triple or aromatic carbon—carbon bonds, as well as carbon-nitrogen bonds, nitrogen—nitrogen bonds, carbon-oxygen bonds and carbon-sulfur bonds. L typically includes ether, thioether, carboxamide, sulfonamide, urea, urethane or hydrazine moieties. Preferred L moieties have 1–20 nonhydrogen atoms selected from the group consisting of C, N, O and S; and are composed of any combination of ether, thioether, amine, ester, carboxamide, sulfonamide, hydrazide bonds and aromatic or heteroaromatic bonds. Preferably L is a combination of single carbon—carbon bonds and carboxamide or thioether bonds. The longest linear segment of the linkage L preferably contains 4–10 nonhydrogen atoms including one or two heteroatoms. Examples of L include substituted or unsubstituted polymethylene, arylene, alkylarylene or arylenealkyl. In one embodiment, L contains 1–6 carbon atoms; in another, L is a thioether linkage. In yet another embodiment, L has the formula —(CH₂)$_a$(CONH (CH₂)$_b$)$_z$—, where a has any value from 0–5, b has any value from 1–5 and z is 0 or 1.

The group $R_x$ is bound to the dye via the linker L at $R^1$, $R^2$, $R^3$, $R^4$, $R^5$, $R^6$, $R^7$, $R^{11}$, $R^{12}$, $R^{13}$, or $R^{14}$. Typically, -L-$R_x$ is bound to the dye at $R^2$, $R^4$ or $R^5$. Preferably -L-$R_x$ is bound to the dye at $R^4$ or $R^5$.

The selection of covalent linkage to attach the dye to the conjugated substance typically depends on the functional group on the substance to be conjugated. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one dye, which may be the same or different, or to a substance that is additionally modified by a hapten. Although some selectivity can be obtained by careful control of the reaction conditions, selectivity of labeling is best obtained by selection of an appropriate reactive dye.

Typically, $R_x$ will react with an amine, a thiol or an alcohol. In one embodiment, $R_x$ is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine, an imido ester, an isocyanate, an isothiocyanate, a maleimide, a phosphoramidite, a sulfonyl halide, or a thiol group. Preferably, $R_x$ is a carboxylic acid, a succinimidyl ester, an amine, a haloacetamide, an alkyl halide, a sulfonyl halide, an isothiocyanate, a maleimide group or an azidoperfluorobenzamido group.

A variety of dye-conjugates may be prepared using the reactive dyes of the invention, including conjugates of antigens, steroids, vitamins, drugs, haptens, metabolites, toxins, environmental pollutants, amino acids, peptides, proteins, nucleic acids, nucleic acid polymers, carbohydrates, lipids, and polymers. In another embodiment, the conjugated substance is an amino acid, peptide protein, polysaccharide, nucleotide, oligonucleotide, nucleic acid, hapten, drug, lipid, phospholipid, lipoprotein, lipopolysaccharide, liposome, lipophilic polymer, polymer, polymeric microparticle, biological cell or virus. In one aspect of the invention, the conjugated substance is labeled with a plurality of dyes of the present invention, which may be the same or different.

The most preferred conjugated substances are conjugates of haptens, nucleotides, oligonucleotides, nucleic acid polymers, proteins, or polysaccharides. Most preferably, the conjugated substance is a nucleic acid, or a substance that interacts in a specific fashion with nucleic acids, such as DNA-binding proteins.

In one embodiment, the conjugated substance ($S_c$) is an amino acid (including those that are protected or are substituted by phosphates, carbohydrates, or $C_1$ to $C_{22}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Also preferred are peptides that serve as organelle localization peptides, that is, peptides that serve to target the conjugated dye for localization within a particular cellular substructure by cellular transport mechanisms. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the conjugated protein is an antibody, an antibody fragment, avidin, streptavidin, a toxin, a lectin, or a growth factor. Preferred haptens include biotin, digoxigenin and fluorophores.

In another embodiment, the conjugated substance ($S_c$) is a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. Preferably, the conjugated nucleotide is a nucleoside triphosphate or a deoxynucleoside triphosphate or a dideoxynucleoside triphosphate.

Preferred nucleic acid polymer conjugates are labeled, single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N—(2-aminoethyl)glycine units, where the nucleic acid contains fewer than 50 nucleotides, more typically fewer than 25 nucleotides. The dye is optionally attached via one or more purine or pyrimidine bases through an amide, ester, ether or thioether bond; or is attached to the phosphate or carbohydrate by a bond that is an ester, thioester, amide, ether or thioether. Alternatively, the dye is attached by formation of a non-covalent association of the nucleic acid an a photoreactive dye of the invention, followed by illumination, resulting in covalently bound dye. Nucleotide conjugates of the invention are readily incorporated by some DNA polymerases and can be used for in situ hybridization and nucleic acid sequencing (e.g., U.S. Pat. Nos. 5,332,666; 5,171,534; and 4,997,928; and WO Appl. 94/05688).

In another embodiment, the conjugated substance ($S_c$) is a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). Preferred polysaccharide conjugates are dextran or FICOLL conjugates.

In another embodiment, the conjugated substance ($S_c$), is a lipid (typically having 6–25 carbons), including glycolipids, phospholipids, and sphingolipids. Alternatively, the conjugated substance is a lipid vesicle, such as a liposome, or is a lipoprotein (see below). Some lipophilic substituents are useful for facilitating transport of the conjugated dye into cells or cellular organelles.

Finally, the conjugates are optionally dye-conjugates of polymers, polymeric particles, polymeric microparticles including magnetic and non-magnetic microspheres, polymeric membranes, conducting and non-conducting metals and non-metals, and glass and plastic surfaces and particles. Conjugates are typically prepared by chemical modification of a polymer that contains functional groups with suitable chemical reactivity. The conjugated polymer may be organic or inorganic, natural or synthetic. In a preferred embodiment, the dye is conjugated to a polymer matrix, such as a polymeric particle or membrane, including membranes suitable for blot assays for nucleic acids or proteins. In another embodiment, the conjugated substance is a glass or silica, which may be formed into an optical fiber or other structure. In another embodiment, the conjugated polymer is poly(ethylene glycol) (Example 19), a poly(acrylate) or a poly(acrylamide).

The preparation of dye conjugates using reactive dyes is well documented, e.g. by R. Haugland, MOLECULAR PROBES HANDBOOK OF FLUORESCENT PROBES AND RESEARCH CHEMICALS, Chapters 1–3 (1996); and Brinkley, BIOCONJUGATE CHEM., 3, 2 (1992). Conjugates typically result from mixing appropriate reactive cyanine dyes and the substance to be conjugated in a suitable solvent in which both are soluble, using methods well known in the art, followed by separation of the conjugate from any unreacted dye and by-products. For those reactive dyes that are photoactivated, conjugation requires illumination of the reaction mixture to activate the reactive dye. The dye-conjugate is used in solution or lyophilized and stored for later use.

Specific binding pair members may be labeled with a dye of the invention and used to detect nucleic acids. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Representative specific binding pairs are shown in Table 3.

TABLE 3

Representative Specific Binding Pairs

| antigen | antibody |
| --- | --- |
| biotin | avidin (or streptayldin or anti-biotin) |
| IgG* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | aDNA (aRNA)† |
| hormone | hormone receptor |
| ion | chelator |

*IgG is an immunoglobulin
†aDNA and aRNA are the antisense (complementary) strands used for hybridization Applications of the Reactive Dyes and Dye-Conjugates Detection of Nucleic Acids The use of invention comprises combining a dye or dye-conjugate of the present invention with a sample that contains or is thought to contain a nucleic acid polymer, incubating the mixture of dye and sample for a time sufficient for the dye to combine with nucleic acid polymers in the sample to form one or more dye-nucleic acid complexes. Typically, the dye-nucleic acid complex will produce a detectable fluorescent signal upon illumination. The characteristics of the dye-nucleic acid complex, including the presence, location, intensity, excitation and emission spectra, fluorescence polarization anisotropy, fluorescence lifetime, and other physical properties of the fluorescent signal can be used to detect, differentiate, sort, quantitate, and/or analyze aspects or portions of the sample. The dyes of the invention are optionally used in conjunction with one or more additional reagents (preferably detectably different fluorescent reagents), including dyes of the same class having different spectral properties.

TABLE 4

Spectral Properties of Selected Dyes of the Invention when bound to DNA*

| Compound No. | Excitation (nm) | Emission (nm) |
| --- | --- | --- |
| 222 | 494 | 516 |
| 513 | 450 | 475 |
| 682 | 476 | 513 |
| 688 | 483 | 518 |
| 1027 | 483 | 515 |
| 1035 | 483 | 515 |
| 1029 | 484 | 516 |
| 1081 | 516 | 555 |
| 1084 | 518 | 549 |
| 1121 | 509 | 530 |
| 1144 | 510 | 528 |
| 1148 | 472 | 495 |
| 6800 | 595 | 617 |
| 65438 | 505 | 532 |
| 65487 | 483 | 521 |

*The dyes of the invention were incubated with double-stranded calf thymus DNA at a dye concentration of 0.1–1 $\mu$M and a DNA concentration of ~50 $\mu$M in TE at pH 7.5 (10 mM Tris-HCl, 1 mM EDTA). Excitation and emission spectra were determined using a spectrofluorometer.

The dyes of the present invention are useful for staining nucleic acids in a variety of environments, and in a variety of assay types, as described previously (U.S. Pat. No. 5,658,751 (1997); incorporated by reference). However, the ability of the reactive dyes of the invention to form covalent attachments to a variety of substances results in their utility for novel and highly useful applications.

Applications of the reactive dyes

The reactive dyes of the invention are particularly useful for immobilizing the dye on a surface or substrate, such as a polymeric microparticle or a polymeric membrane. In this embodiment, the dye is useful as a high affinity nucleic acid capture reagent for purification or detection of nucleic acids. Alternatively, the immobilized dyes are useful for moving associated nucleic acids from one environment to another via mechanical means. Where the subject dyes are attached to a surface, the surface can also function as a quantitative or qualitative indicator of nucleic acids in solution, such as a test strip or dipstick.

The immobilized nucleic acids could also be used to analyze nucleic acid-protein interactions. In this embodiment, immobilized dye is used to capture nucleic acids and hold them in place, allowing free proteins to interact with the bound nucleic acids. Where the protein binds with immobilized nucleic acid, the proteins themselves can be eluted (for example with salt, detergent, or chaotropes such as NaI) and analyzed.

The reactive dyes of the invention are also useful as detection reagents during the separation and purification of nucleic acids. For example the dyes of the invention can be conjugated to agar or agarose (Example 24) and used to cast plates or gels that are then useful for spot assays to quantitate nucleic acids. The ability of the reactive dyes of the invention to form stable covalent bonds with a variety of substrates allows the attachment of nucleic acid stains to electrophoretic gel matrices (producing very stable and uniformly stained preprepared gels).

Alternatively, where nucleic acids are analyzed using capillary electrophoresis, the dyes of the invention may be conjugated in a small "band" or region in the capillary, resulting in detection of nucleic acids with high sensitivity, as the detecting reagent is concentrated into a small volume, allowing efficient illumination using a laser or other excitation source. Where a conjugated dye is used in this fashion, the dye is optionally utilized only to capture the nucleic acids, with detection accomplished by another detection reagent, or the fluorescent enhancement upon binding nucleic acids is utilized to detect the capture event itself.

Where the dye is covalently bound to a substrate, such as a polymeric microparticle or membrane, the nucleic acids that are associated with the bound dye can be used as templates for translation and replication. Where the dye of the invention possesses a particularly high affinity for nucleic acids, passing a solution containing nucleic acids over a suitable labeled polymer matrix results in depletion of nucleic acids from the solution (Example 24). The complexed nucleic acids can then be utilized in place or extracted from the matrix for further analysis or utilization.

Alternatively, a reactive dye of the invention can be associated with purified nucleic acids and covalently linked to the nucleic acids, which are then transferred to a membrane by blotting, and covalently bound to the polymeric membrane, resulting in a permanently labeled blot.

A dye-labeled protein or drug can also be used as a probe for transport mechanisms by incubating the labeled probe with cells of interest. Transport of the probe to the nucleus, or any other portion of the cell that contains nucleic acids, would result in fluorescence enhancement, and localization of the probe would be detected. For example, dexamethasone interactions with glucocortacoid receptors could be studied in this manner.

The dyes are optionally covalently bound to a molecule, such as a dextran, which is normally excluded from live cells. When dead or permeabilized cells then take up these molecules, the bound dye interacts with intracellular nucleic acids, giving rise to fluorescence. Similarly, the dye-conjugates of the invention possess utility for retaining conjugated substances within cells. This is particularly useful for conjugated substances that are typically excreted from living cells relatively quickly, such as small organic molecules or by-products of enzyme activity.

The dye is optionally conjugated to a substance selected such that the resulting conjugate has substantially different physical properties than those of the unbound dye. For example, conjugation of a dye of the invention to poly (ethylene glycol) polymer results in a dye that exhibits very little fluorescence enhancement in the presence of albumin, whereas the free dye binds non-specifically with albumins exhibiting fluorescence enhancement.

Applications of covalently labeled nucleic acids

The dyes of the invention are useful for labeling unmodified nucleic acids covalently (typically using a photoreactive dye, as in Example 21) so that the labeled nucleic acid retains its label through capillary transfer or electrophoretic transfer to filter membranes and subsequent hybridization (for example as in Southern blotting). The dyes are also useful in Southwestern analysis, wherein the dye is first coupled covalently to a nucleic acid, and the nucleic acid is then used to probe a Western blot containing putative nucleic acid-binding proteins (Example 26). Fluorescence enhancement indicates locations on the blot membrane where the nucleic acid has been captured by the immobilized protein. Conjugates of proteins that do not interact specifically with nucleic acids do not exhibit similar fluorescence enhancement when used at similar concentrations (Example 22, FIG. 2). Similar interactions are useful for detecting immobilized DNA (Example 25). Alternatively, where the protein is labeled with a second reagent, colocalization of that reagent and the dye of the invention indicates an interaction between the dye and the protein. This type of assay is also useful for analyzing nucleic acid-binding drugs.

Where the dyes of the invention are used to covalently label nucleic acids, the labeled nucleic acid is useful as a probe to detect interactions between nucleic acid-binding drugs or proteins, where the drug or protein has been labeled with a second fluorophore or a fluorescence quenching agent. Binding of the nucleic acid with the drug or protein results in loss of fluorescence. In this way, the nucleic acid-binding drug or protein can be quantitated, and the presence or absence of either inhibitors or enhancers of nucleic acid binding could be identified. This application is also useful for in vivo or in vitro studies, for example in the study of interactions between SSB (single strand binding protein) and single stranded DNA, histones and double stranded DNA, sequence specific binding factors and their cognate sequences, or mismatch repair enzymes and mismatch regions of DNA hybrids.

Dye-labeled nucleic acids are useful for monitoring transfection into cells, either by the labeled nucleic acid itself, or where another molecule is cotransfected and the labeled nucleic acid is simply a tracer. The amount of labeled nucleic acid in a cell could be used to standardize the copy number of transiently transfected plasmids in reporter gene assays, such as chloramphenicol acetyltransferase assays (CAT assays).

Dye-conjugates of nucleic acids possess utility for detecting hybridization, as the dye-conjugate typically exhibits a change in fluorescence enhancement upon binding to a complementary strand of nucleic acid (Example 23). Dye-labeled nucleic acids are also useful for following triplex formation, or strand invasion, during DNA recombination. If two dyes capable of energy transfer are used, then real-time measurements of hybridization or strand invasion/ displacement may be made. In particular both the interactions of a antisense oligonucleotides with nucleic acids and RNA splicing could be followed using this methodology.

Where the dye is used to covalently label a nucleic acid, the nucleic acid could then be ligated to another unlabeled nucleic acid, so that even if the labeled nucleic acid fragment is unable to hybridize or bind proteins efficiently, the unlabeled portion retains full biological activity. However, the nucleic acid is readily detectable due to the presence of the attached dye.

The dyes of the invention also serve as haptens for secondary detection. The use of labeled antibodies directed against the dyes of the invention allows for signal amplification in the detection of either a conjugated substance, or a labeled nucleic acid. Alternatively, where the conjugated substance is a specific binding pair member, the specific binding pair member may be used to amplify the detectable signal of the cyanine dye, typically by immunological methods. In this embodiment, the conjugated substance is typically a hapten, biotin or digoxigenin or a non nucleic acid-binding dye. The dye-conjugate forms a nucleic acid-dye complex, producing enhancement of its fluorescence. The complex is then labeled with the complement of the specific binding pair member, which is typically labeled with a fluorophore, producing an additional fluorescent enhancement.

Synthesis

Synthesis of unsymmetrical cyanine dyes, including cyanine dyes having cyclic substituents or TAIL moieties has been described previously (U.S. Pat. No. 5,436,134 to Haugland et al. (1995); U.S. Pat. No. 5,658,751 to Yue et al. (1997), supra). The synthetic route to the dyes of the present invention requires the synthesis of three precursors: an appropriate benzazolium salt, an appropriate pyridinium (or quinolinium) salt (both of which have the appropriate chemical substituents, or can be converted to the appropriate substituents), and (where n=1 or 2) a source for the methine spacer.

The pyridinium or quinolinium moiety

In the synthesis of the dyes of the invention, the second heterocyclic precursor is usually a pyridinium salt that is already appropriately substituted. Alternatively, substituents can be incorporated into the pyridinium structure subsequent to attachment of the benzazolium portion of the dye. Such substituents include TAIL moieties or reactive functional groups.

Aside from the structural differences between pyridines and quinolines, there exist two major structural distinctions within the family of dyes described in the invention, related to the point of attachment of the pyridinium moiety. In one case (where m=0 and p=1) the position of attachment places the methine bridge adjacent to the ring nitrogen (2-pyridines). In the more common case (where m=1 and p=0) the position of the nitrogen atom is para to the point of attachment (4-pyridines).

Typically the required pyridinium salt precursor has the structure

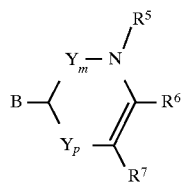

and the quinolinium salt precursor has the general structure

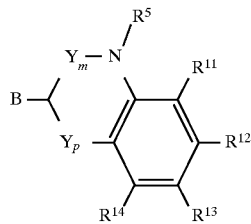

with the substituents as defined previously. At all times, the ring is a 6-membered pyridinium-based heterocycle.

When n=0, B is methyl, or B is chloro, bromo or iodo. When n1 or 2, B is methyl.

There are several general methods for the synthesis of derivatives of pyridinium, including those derivatives having substituents at any available position, including substitutions that are reactive function groups, or that can be converted to reactive functional groups before or after reaction with the benzazolium portion to form the dye core structure.

Alkylation of the nitrogen atom of an appropriately substituted quinoline with an alkylating agent directly yields a substituted quinolinium salt. Selection of an appropriate alkylating agent provides a substituent at $R^5$ that is a TAIL moiety or reactive group, or a precursor for a TAIL moiety or a reactive group.

$R^5$ substituents that are aryl or heteroaryl are best incorporated by an Ullmann reaction of aniline or a substituted aniline or of a pyridone or quinolone derivative. In this method, a diaryl amine or aryl-heteroaryl amine (generally commercially available) is condensed with diketene and acid to yield a 4-methyl-N-arylquinolone or a 4-methyl-N-heteroarylquinolone. The 4-methyl-2-quinolone is then converted to the desired 4-methyl-2-substituted-quinolinium salt by reaction with an organometallic reagent such as a Grignard or organolithium reagent. An $R^4$ substituent attached in this way may be aromatic or aliphatic, can be a TAIL or a TAIL precursor, or can be a reactive group ($R_x$) or reactive group precursor, provided that the nature of the substituent does not interfere with preparation of the required organometallic reagent. Pyridone and quinolone precursors may also be prepared by an Ullmann reaction of the appropriately substituted precursor if the nitrogen atom is hydrogen-substituted. While a variety of 4-methyl-2-quinolones are commercially available, desired derivatives can be synthesized by reaction of aniline or a substituted-aniline with an acetoacetate or acetoacetate equivalent reagent such as diketene.

Pyridone and quinolone intermediates containing a non-hydrogen group at $R^5$ are particularly important precursors to a wide variety of other pyridinium and quinolinium salts that are substituted at $R^4$. In particular, a salt is formed by treatment of the appropriate pyridone or quinolone with a strong chlorinating agent such as $PCl_5$, $POCl_3$ or $SOCl_2$.

Halogen displacement

The reactivity of the 2-halogenated pyridinium or quinolinium intermediate offers a variety of synthetic methods for attachment of various substituents at the 2-position, including TAIL moieties, TAIL precursors, reactive groups or reactive group precursors. However, the reactivity of the 2-halo derivatives is preserved even after conjugation with the benzazolium precursor, enabling conversion of the resulting dye in which $R^4$ is halogen into the appropriate alkoxy, amino and thiolate analogs, as described for the pyridinium and quinolinium precursors. Of particular utility for the dyes of the present invention is the displacement of a 2-chloro substituent by an amine, thiol or alcohol, resulting in post-condensation substitution of a TAIL or reactive group.

Additionally, the 2-oxo group of pyridone or quinolone precursors can be chemically reduced to derivatives in which $R^4$ is H using a variety of reagents including DIBAL-H (diisobutylaluminum hydride).

Synthesis of TAIL moieties

As described earlier, TAIL is composed of three parts: LINK, SPACER and CAP. If a TAIL is present as $R^5$, then LINK is constrained to be a single bond, eliminating the potential of N—S, N—O or N—N bonds in TAIL. The chemical composition of SPACER is determined by the chemistry required to attach the heteroatom in CAP with the dye core structure via LINK.

As described above, those dyes of the present invention that are 4-pyridiniums or 4-quinoliniums wherein $R^4$ is a TAIL are most conveniently synthesized from the 2-halopyridinium or 2-haloquinolinium precursor either before or after condensation with the benzazolium portion of the dye by a nucleophilic displacement reaction of the halogen by a thiol, alkoxide, or a primary or secondary amine.

CAP may be incorporated directly into TAIL before or after condensation of the pyridinium or quinolinium salt with the benzazolium salt, or CAP may be added or further modified at a later stage in the synthesis. For instance, when CAP is a cyclic or non-cyclic primary, secondary or tertiary amine, CAP can be alkylated to a quaternary ammonium.

Precursors to TAIL include carboxylic acids, halides, alcohols and thiols. Each of these reactive groups can be used to attach a heteroatom containing moiety (i.e., CAP) to the dye's core structure, generally through the formation of amides, ethers or thioethers, which are incorporated into SPACER before or after attachment of SPACER to the dye's core structure.

Synthesis of -L-$R_x$ moieties

As described for TAIL moieties above, -L-$R_x$ moieties are typically prepared from 2-halopyridinium or 2-haloquinolinium precursor either before or after condensation with the benzazolium portion of the dye by a nucleophilic displacement reaction of the halogen by a thiol, alkoxide, or a primary or secondary amine, which is then incorporated into the covalent linkage L.

As described above, methods of preparing chemically reactive functional groups are well known in the art (Haugland, MOLECULAR PROBES HANDBOOK OF FLUORESCENT PROBES AND RESEARCH CHEMICALS, Chapters 1–3, (1996)). Some examples of this type of conversion include:

1. The activation of amine groups to yield reactive species, including isocyanates, isothiocyanates, 4,6-dichloro-1,3,5-triazines, maleimides or haloacetamides;
2. The conversion of carboxylic acid groups to activated derivatives, including symmetric and mixed anhydrides, acid halides, acyl azides, acyl hydrazides and various activated esters, including succinimidyl esters, p-nitrophenyl esters and pentafluorophenyl esters;
3. The conversion of sulfo groups to sulfonyl chlorides and sulfonyl fluorides;
4. The conversion of alcohols groups to ethers, esters, urethanes, carbonates or alkylating agents that include sulfonate esters and halides;
5. The conversion of thiols to thioethers, thioesters and disulfides;

Condensation of the dye

The benzazolium precursors are prepared and condensed with the pyridinium or quinolinium salts according to the synthetic procedures outlined in U.S. Pat. No. 5,436,134 to Haugland et al. (1995). The specific method of conjugation and reagents used result in a methine, trimethine or pentamethine bridge between the two ring systems.

The examples below are given so as to illustrate the practice of this invention. They are not intended to limit or define the entire scope of this invention.

EXAMPLES

Example 1

Preparation of 2-(3-carboxyethylthio)-4-(2,3-dihydro-3-methyl-(benzo-1,3-thiazol-2-yl)methylidene)-1-phenylquinolinium iodide (Compound 1121):

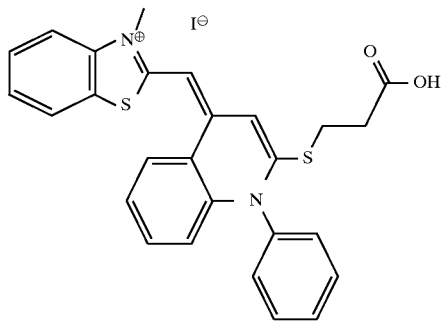

To 2.2 g (5 mmol) of 2-chloro-4-(2,3-dihydro-3-methyl-(benzo-1,3-thiazol-2-yl)methylidene)-1-phenylquinolinium chloride and 0.24 mL (5.5 mmol) of 3-mercaptopropionic acid in 70 mL of methylene chloride is added 1.54 mL of triethylamine and the mixture is stirred at room temperature for 10 min. The solvent is evaporated and the residue is dissolved in 80 mL of 1:1 DMF/methanol and added to 2.5 g of 57% HI in 400 mL of water. The precipitate is collected and purified by recrystallization from DMF/ethyl acetate. Ex/Em=509/530 nm when bound to ds DNA.

Example 2

Preparation of 2-(3-succinimidyloxycarbonylethylthio)-4-(2,3-dihydro-3-methyl-(benzo-1,3-thiazol-2-yl)methylidene)-1-phenylquinolinium iodide (Compound 1144):

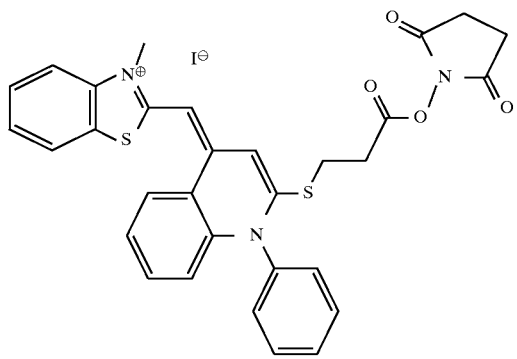

A solution of 1.0 g (1.7 mmol) of Compound 1121 (Example 1), 1.72 g (8.3 mmol) of dicyclohexylcarbodiimide (DCC) and 0.96 g (8.3 mmol) of N-hydroxysuccinimide is stirred at room temperature overnight, 320 mL of ethyl acetate is added and the resulting precipitate is chromatographed on silica gel. Ex/Em=510/528 nm when bound to ds DNA.

Example 3

Preparation of 2-((N-3-carboxypropyl-N-methyl)amino)-4-(2,3-dihydro-3-methyl-(benzo-1,3-thiazol-2-yl)methylidene)-1-phenylquinolinium iodide (Compound 1027):

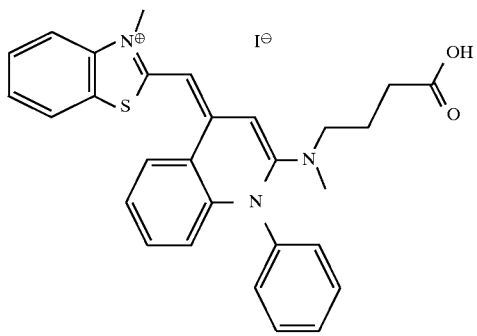

A solution of 0.69 g (4.5 mmol) of 4-(methylamino) butyric acid hydrochloride, 0.75 g (5 mmol) of t-butyldimethylsilyl chloride and 1.9 mL of triethylamine in 50 mL of methylene chloride is stirred for 4 hr. 0.66 g (1.7 mmol) of 2-chloro-4-(2,3-dihydro-3-methyl-(benzo-1,3-thiazol-2-yl)-methylidene)-1-phenylquinolinium chloride is added and the reaction is heated at 60° C. for 1 hr. The solvent is evaporated, the residue is dissolved in 40 mL of DMF and 5 mL of methanol and is added to a solution of 6.0 g of NaI and 4.0 g of 57% HI in 270 mL of water. The resultant precipitate is collected and dried. Ex/Em=483/515 nm when bound to ds DNA.

Example 4

Preparation of 2-((N-3-succinimidyloxycarbonylpropyl-N-methyl)amino)-4-(2,3-dihydro-3-methyl-(benzo-1,3-thiazol-2-yl)methylidene)-1-phenylquinolinium iodide (Compound 1029):

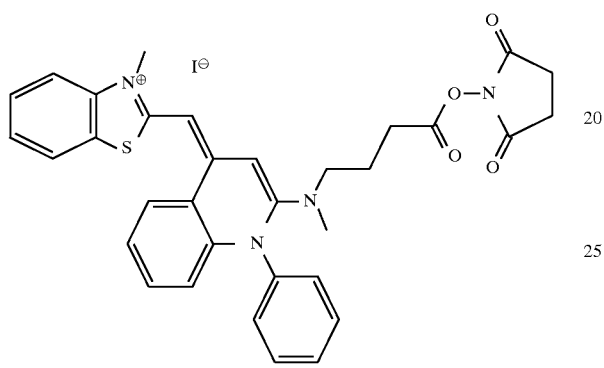

A solution of 0.38 g (0.625 mmol) of Compound 1027 (Example 3), 1.2 g (6.25 mmol) of 1-ethyl-3-(3-dimethylaminopropyl)carbodiimide hydrochloride, 0.72 g (6.25 mmol) of N-hydroxysuccinimide and 3 mL of pyridine in 15 mL of DMSO is stirred at room temperature overnight. Concentration at 30° C. to remove the pyridine and addition to 100 mL of water containing 8 g of NaI and 5 g of 57% HI results in crude product, which is recrystallized from DMF/ethyl acetate. Ex/Em=484/516 nm when bound to ds DNA.

Example 5

Preparation of 2-(4-aminophenylthio)-4-(2,3-dihydro-3-methyl-(benzo-1,3-thiazol-2-yl)methylidene)-1-phenylquinolinium iodide (Compound 1079):

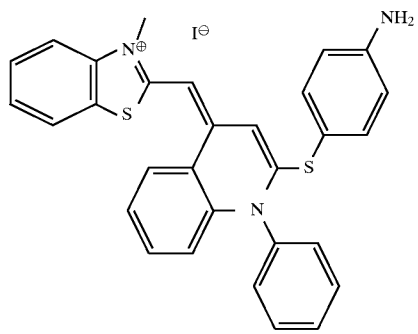

This compound is prepared as in Example 1 using 4-aminothiophenol instead of 3-mercaptopropionic acid.

Example 6

Preparation of 2-(4-isothiocyanatolphenylthio)-4-(2,3-dihydro-3-methyl-(benzo-1,3-thiazol-2-yl)methylidene)-1-phenylquinolinium iodide (Compound 1084):

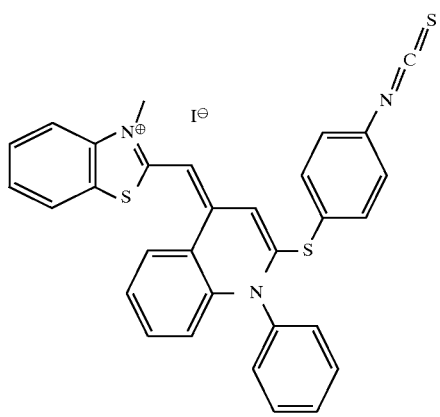

A solution of 53 mg of Compound 1079 (Example 5) and 12 μL of thiophosgene in 1 mL of DMF is stirred at room temperature for one hour and 3 mL of ethyl acetate is added to precipitate the product. Ex/Em=518/549 nm when bound to ds DNA.

Example 7

Preparation of 2-butyl-4-(2,3-dihydro-3-methyl-(benzo-1,3-thiazol-2-yl)methylidene)-1-(4-aminophenyl)quinolinium iodide (Compound 10103):

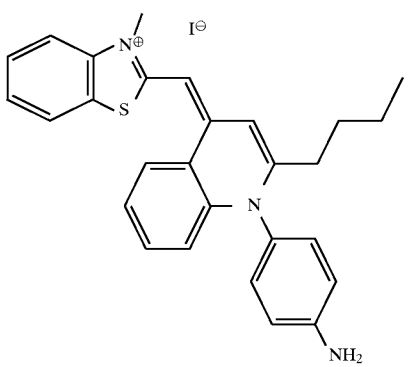

To a solution of 0.25 g (1 mmol) of 1-(4-aminophenyl)-1,2-dihydro-4-methyl-2-quinolone in 20 mL of TEF at −78° C. is added 1.5 mL of 2.5M (3.75 mmol) n-butyl lithium in TBF. After one hour 0.4 mL of acetic acid is added, the reaction is warmed to room temperature and stirring is continued for 3 hr. Evaporation to dryness is followed by addition of 20 mL methylene chloride and 0.367 g (1 mmol) of 3-methyl-2-methylthiobenzothiazolium tosylate and 0.56 mL of triethylamine and stirring for 2 hours. The reaction mixture is evaporated to dryness, dissolved in 5 mL of DMF and the solution is added to 1.7 g of NaI in 90 mL of water to give the solid product.

Example 8

Preparation of 2-(9-mercaptononylthio)-4-(2,3-dihydro-3-methyl-(benzo-1,3-thiazol-2-yl)methylidene)-1-phenylquinolinium iodide (Compound 65438):

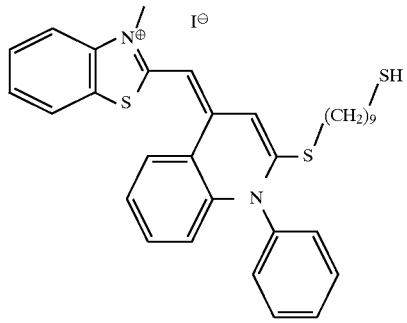

Compound 65438 is prepared as in Example 1 using 1,9-nonanedithiol instead of 3-mercaptopropionic acid. Purification is accomplished via silica gel chromatography. Ex/Em=505/532 nm when bound to ds DNA.

Example 9

Preparation of 2-(2-carboxyethylthio)-4-(2,3-dihydro-3-methyl-(benzo-1,3-oxazol-2-yl)methylidene)-1-phenylpyridinium iodide (Compound 513):

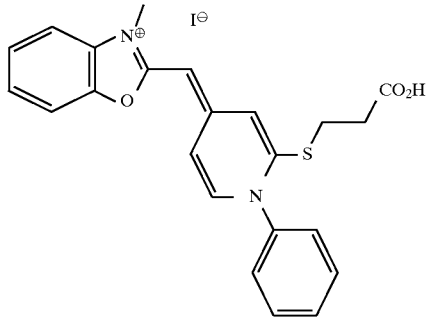

Compound 513 is prepared as in Example 1 using 2-chloro-4-(2,3-dihydro-3-methyl-(benzo-1,3-oxazol-2-yl)methylidene)-1-phenylpyridinium chloride instead of the quinolinium chloride. Ex/Em=450/475 nm when bound to ds DNA.

Example 10

Preparation of 2-(4-iodoacetamidophenylthio)-4-(2,3-dihydro-3-methyl-(benzo-1,3-thiazol-2-yl)methylidene)-1-phenylquinolinium iodide (Compound 1081):

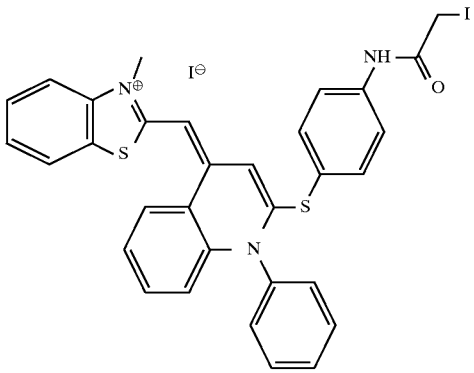

To 53 mg of Compound 1079 (Example 5) in 1 mL of DMF is added 21 μL of diisopropylethylamine and 31 mg of succinimidyl iodoacetate. The solution is heated for 16 hours at 35° C. A further 62 mg of the succinimidyl iodoacetate and 42 μL of diisopropylethylamine is added followed by heating at 35° C. for 24 hours. Addition of 3 mL of DMF and filtration of the product gives 27 mg of Compound 1081. Ex/Em=516/555 nm when bound to ds DNA.

Example 11

Preparation of 2-(4-azido-2-nitrophenylaminoethylamino)-4-(2,3-dihydro-3-methyl-(benzo-1,3-thiazol-2-yl)methylidene)-1-phenylquinolinium iodide (Compound 682):

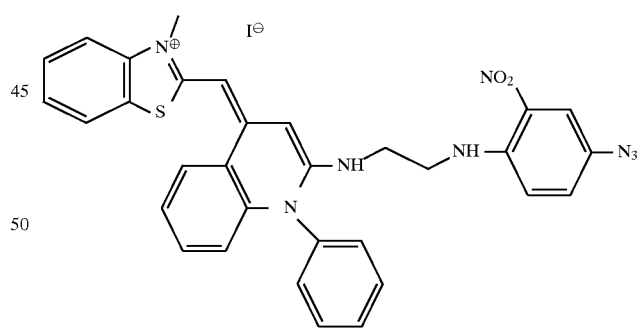

A mixture of 30 mg of 2-chloro-4-(2,3-dihydro-3-methyl-(benzo-1,3-thiazol-2-yl)methylidene)-1-phenylquinolinium chloride and 38 mg of 2-(2'-aminoethylamino)-5-azidonitrobenzene and 8 μL of triethylamine is heated at 55° C. for 2 hr. The solvent is evaporated, and the residue is dissolved in 2 mL of DMF and added to a solution of 0.2 g of NaI in 15 mL of water. The resulting precipitate is collected and dried under vacuum. The crude product is recrystallized from MeOH as the iodide salt. Ex/Em=420/489 nm when bound to ds DNA.

Example 12

Preparation of 2-(4-azido-2,3,5,6-tetrafluorobenzoyl-N-methylaminopropyl-N'-methylamino)-4-(2,3-dihydro-3-methyl-(benzo-1,3-thiazol-2-yl)methylidene)-1-phenylquinolinium iodide (Compound 688):

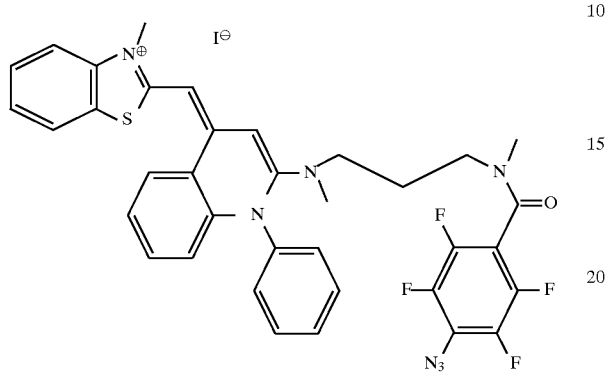

Compound 688 is prepared as in Example 11 using N-(2-(N'-methylamino)ethyl)-N-methyl-2,3,5,6-tetrafluoro-4-azidobenzamide. The crude product is recrystallized from MeOH. Ex/Em=483/518 nm when bound to ds DNA; NMR (ppm) 8.64 (1H,d), 7.95 (1H,d), 8.3–7.5 (9H,m), 7.36 (1H,t), 7.0 (1H,s), 6.8 (1H,s), 4.0 (3H,s), 3.4 (2H,t), 3.35 (2H,t), 2.9 (3H,s), 2.86 (3H,s).

Example 13

Preparation of 2-(4-azido-2-nitrophenyl-N-ethylaminopropyl-N'-ethylamino)-4-(2,3-dihydro-3-methyl-(benzo-1,3-thiazol-2-yl)methylidene)-1-phenylquinolinium chloride (Compound 222):

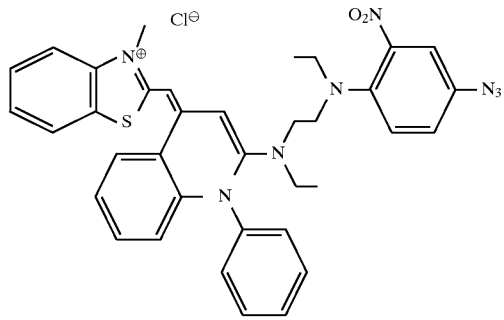

Compound 222 is prepared as in Example 11 using 2-{N-[3-(N'-ethylamino)propyl]-N-ethyl}amino-5-azidonitrobenzene and 1,2-dichloroethane as the solvent. Evaporation of the reaction mixture is followed by purification by column chromatography. Ex/Em=494/516 nm when bound to ds DNA.

Example 14

Preparation of 2-(N,N'-dimethylhydrazino)-4-(2,3-dihydro-3-thiazol-2-yl)methylidene)-1-phenylqiuinolinium chloride (Compound 65487):

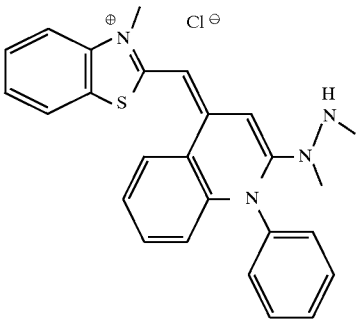

Compound 65487 is prepared as in Example 11. A mixture of the 2-chloro derivative and N,N'-dimethylhydrazine is heated in DMF at 60° C. for 2 hours. Filtration of the crude product and column chromatography gives the desired product. Ex/Em=483/521 nm when bound to ds DNA.

Example 15

Preparation of 2-(2-chloroethylaminocarbonylpropyl-N-methylamino)-4-(2,3-dihydro-3-methyl-(benzo-1,3-thiazol-2-yl)methylidene)-1-phenylquinolinium iodide (Compound 1035):

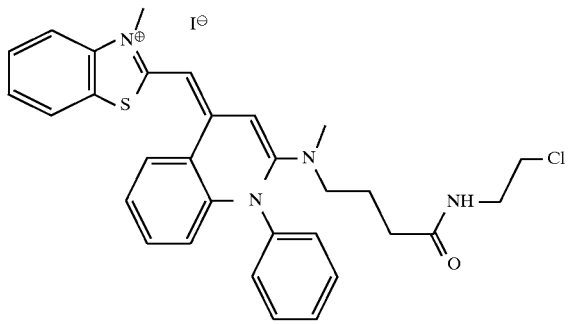

To a solution of 7 mg of Compound 1029 (Example 4) and 4 mg of 2-chloroethylamine hydrochloride in 0.3 μL of DMF is added 10 mL of triethylamine. After 10 min the reaction mixture is added dropwise to 0.5 g of NaI in 2 mL of water. The product is recovered by filtration. Ex/Em=483/515 nm when bound to ds DNA.

Example 16

Preparation of 2-(7-amino-4-methyl-4-azaheptylimino)-4-(2,3-dihydro-3-methyl-(benzo-1,3-thiazol-2-yl)methylidene)-1-phenyl-1,2-dihydroquinoline (Compound 1148):

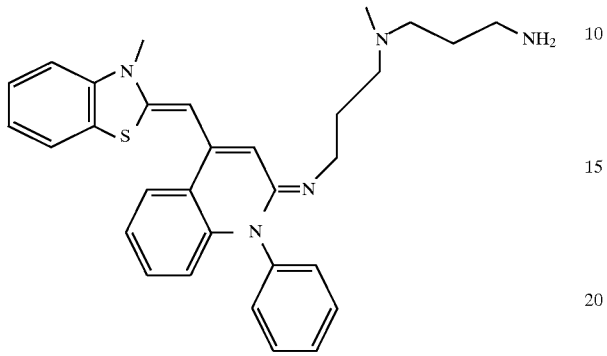

Compound 1148 is prepared as in Example 11 using 3,3'-diamino-N-methyldipropylamine and stirring at room temperature for 15 min. The crude product obtained from the NaI workup is recrystallized from DMF-EtOAc. Ex/Em= 472/495 nm when bound to ds DNA.

Example 17

Preparation of 2-(2-carboxyethylthio)-4-(2,3-dihydro-3-methyl-(benzo-1,3-thiazol-2-yl)propylidene)-1-phenylpyridinium chloride (Compound 6800):

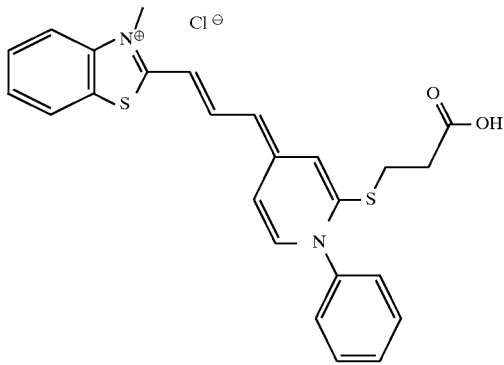

Acetic anhydride (0.2 mL) is added to a mixture of 420 mg of 2-chloro-4-methyl-1-phenylpyridinium chloride, 880 mg of 2-(2-anilinovinyl)-3-methyl benzothiazolium p-toluenesulfonate and 0.83 mL of triethylamine in 20 mL of methylene chloride. After 10 min a solution of 0.52 mL of 3-mercaptopropionic acid and 0.8 mL of triethylamine in 10 mL of methylene chloride is added, the reaction mixture is stirred for 30 min and poured into 60 mL of 1M HCl. The product is collected by filtration. Ex/Em=595/617 nm when bound to ds DNA.

Example 18

Preparation of 2-butyl-4-(2,3-dihydro-3-(3-carboxypropyl-(benzo-1,3-thiazol-2-yl)methylidene))-1-phenylquinolinium iodide (Compound 6900):

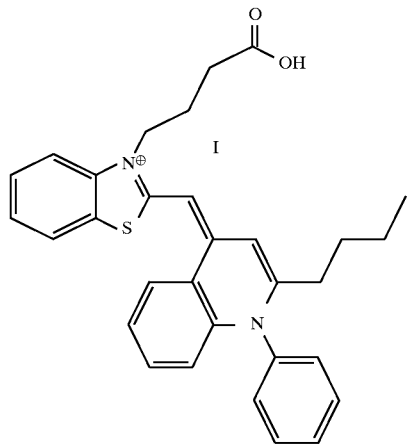

To a mixture of one equivalent of 3-(3-ethoxycarbonylpropyl)-2-(3-ethoxycarbonylpropylthio)-benzothiazolium bromide and 2-butyl-3-methyl-1-phenylquinolinium acetate in methylene chloride, one equivalent of triethylamine is added and the resulting solution is stirred at room temperature overnight. The resulting ethyl ester is then hydrolyzed with 10% lithium hydroxide in DMF to obtain Compound 6900.

Example 19

Preparation of a poly(ethylene glycol) conjugate of Compound 1029:

To a solution of 5.3 mg of Compound 1029 (Example 4) and 25 mg of poly(ethylene glycol) methyl ether, amine-terminated (average MW 5000, Molecular Probes, Inc.) in 2 mL of DMF, 0.1 mL of pyridine is added and the resulting solution is stirred at room temperature overnight. The solvent is removed under vacuum and the residue is purified on silica gel.

Example 20

Preparation of a biotin conjugate of Compound 1148:

To Compound 1148 and 1 equiv. of 6-((biotinoyl)amino) hexanoic acid, succinimidyl ester in 1 volume of DMF at room temperature, 1 equiv. of triethylamine is added and the mixture is stirred for 2 hours. The reaction mixture is then added dropwise into 6 volumes of $H_2O$ and the resulting product is recovered by filtration.

Example 21

Photoaffinity labeling of DNA in solution:

Tris buffer and other free amines are removed from DNA samples by several ethanol precipitations. Approximately 2.5 µg double-stranded DNA is incubated with 300 µM Compound 688 (Example 12) in 50–100 µL water for 20–40 minutes, protected from light. The vial containing the mixture is then inverted on an ultraviolet transilluminator and irradiated for 1 minute at a wavelength of 300 nm. Approximately ¹⁄₁₀th volume of 1M NaCl and 2.5 volumes of ethanol are added to the sample, which is then mixed and allowed to precipitate for 30 minutes at −20° C. Labeled DNA is pelleted by centrifugation and resuspended in 10 mM Tris-HCl, pH 7.5, 1 mM EDTA (TE). The ethanol precipitation process is repeated twice, pellets are washed twice in 70% ethanol, and the DNA dissolved in TE. The resulting labeled DNA exhibits fluorescence at 515 nm after excitation at 485 nm, whereas DNA that has been incubated in the presence of SYBR Green I nucleic acid stain, which cannot be used as a photoaffinity label, is not fluorescent.

For example, calf thymus DNA is incubated with Compound 688 or with SYBR Green I nucleic acid stain (open symbols) according to the procedure described above. Samples are treated with light for 0, 15, 30 or 60 seconds and purified as described. The fluorescence of the samples is measured at 490–700 nm after excitation at 485 nm. Integrated fluorescence values are plotted versus time of illumination (FIG. 1). Compound 668 forms light-dependent irreversible DNA complexes (♦), while SYBR Green I stain can be removed from DNA with ethanol precipitation whether or not the complex has been light-treated (□).

Example 22

Labeling proteins and use of labeled proteins to detect protein-nucleic acid interactions in solution:

A 200 μL sample containing 600 μg calf thymus histones (type IIIss, Sigma) or bovine serum albumin (BSA) in PBS (phosphate-buffered saline) is placed in a vial containing a stir bar and 20 μL freshly prepared 1M sodium bicarbonate (pH 8.3) is added. Compound 1029 or Compound 1144 is freshly dissolved in anhydrous DMSO at a concentration of 28.5 mM and 8 μL of the dye solution is added to the protein solution to achieve a molar dye:protein ratio of 5:1, with stirring. The reaction mixture is stirred for 1–1.5 hours, protected from light, at room temperature. Hydroxylamine (8 μL; 5M; pH 8.5), is added to the reaction and stirring is continued for 15 minutes more. Unbound dye is removed from the conjugate by size exclusion chromatography, using SEPHADEX G15 resin (Sigma) and PBS.

Figure 2:
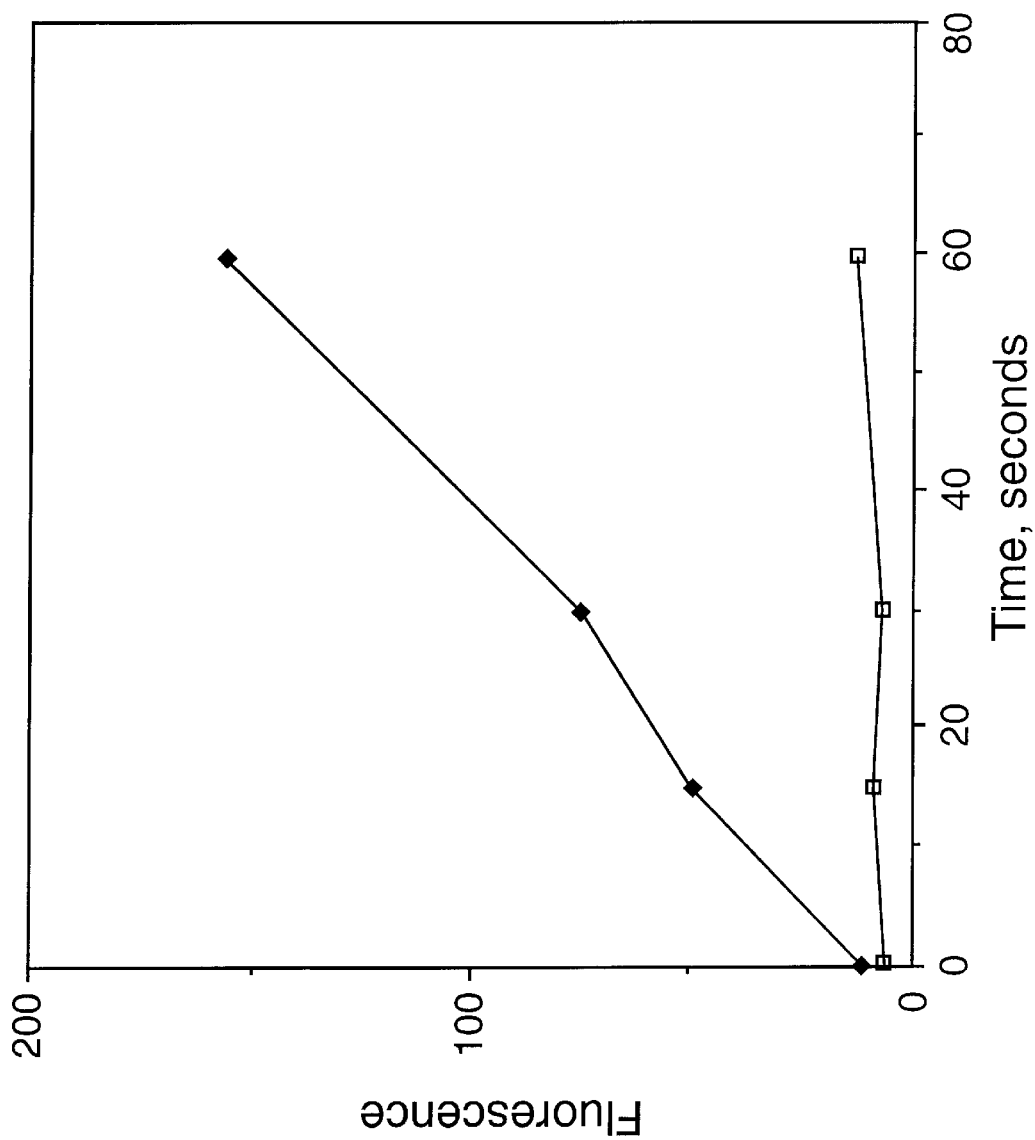
FIG. 2: Detection of protein-nucleic acid interactions in solution, using histones labeled with a dye of the present invention, as described in Example 22.

The resulting conjugates exhibit increased fluorescence relative to free dye, but this fluorescence is at longer wavelengths than the fluorescence observed for dye bound to DNA at low dye:bp ratios. When incubated with double-stranded calf thymus DNA, histone conjugates show >20-fold increase in fluorescence intensity and the fluorescence emission is at the same wavelengths as are observed for unconjugated dye bound to DNA at low dye:bp ratios. Thus the conjugated dye serves as an indicator for the histone-DNA interaction (FIG. 2).

Example 23

Labeling oligonucleotides and use of labeled oligonucleotides in hybridization assays:

HPLC-purified, amine-modified oligonucleotide (100 μg) is dissolved in 18 μL distilled, deionized water. A solution of 50 mM Compound 1029 or 1144 in anhydrous DMSO is prepared and 7 μL dye is added to the oligonucleotide. Freshly prepared 0.1M sodium borate, (75 μL; pH 8.5) is added to each vial, the contents are mixed, and the reaction is incubated overnight at room temperature, with gentle agitation, protected from light. ¹⁄₁₀th volume 3M NaCl and 2.5 volumes of absolute ethanol are added, the sample is mixed, and the nucleic acids allowed to precipitate for 2 hours at −20° C. Nucleic acids are pelleted in a microcentrifuge and the pellet washed twice with 70% ethanol. The pellet is air-dried. Dye conjugates are purified on a C8 HPLC column, using a gradient of 5–95% acetonitrile in 0.1M triethylammonium acetate. Residual solvent is evaporated from nucleic acids and they are resuspended in water. This solution is extracted with chloroform and precipitated again with ethanol as above.

Dye-conjugated oligonucleotides are hybridized with their reverse complement or with complimentary DNA using standard procedures. Although dye-conjugates exhibit fluorescence in solution, there is a fluorescence increase upon hybridization to the complementary DNA strand.

Example 24

Labeling amino-agarose and use of dye-agarose to deplete solutions of DNA:

Amino agarose is prepared by oxirane activation of agarose (SEPHAROSE CL-2B, Sigma) as described in Dean et al. (AFFINITY CHROMATOGRAPHY, A PRACTICAL APPROACH, IRL Press, (1985) pp 34–35), except that the activated agarose is incubated 5 hours at 55° C. with concentrated ammonium hydroxide, and then washed extensively with water and equilibrated in PBS. Seven mL of amino agarose resin is washed with 50 mL 0.15M NaHCO₃. The resin is suspended in 3.5–4 mL NaHCO₃ and placed in an amber vial. A solution containing 11.2 mM Compound 1029 dye in anhydrous DMSO is freshly prepared and 1 mL of the dye solution is added to the resin slurry. The resulting mixture is rotated slowly on a wheel at room temperature for 3 hours. Acetic anhydride (125 μL) and 6M NaOH (450 μL) are added; the resin is mixed and loaded immediately onto a 5 mL column and washed extensively with 0.15M NaHCO₃ to remove unbound dye. Approximately 225 μL of the resin is transferred to a 2 mL BioRad minicolumn.

DNA is depleted from a solution as follows. Double-stranded calf thymus DNA (4–6 μg) that has been sheared by passage through a narrow gauge needle is applied to the column in 600 μL TE. The column flow-through is collected. The column is washed with ~900 μL TE and the wash is collected. Absorbance measurements indicate that the DNA is depleted from the solution.

Example 25

Detecting DNA immobilized on filter membranes using dye-protein conjugates:

Conjugates of proteins are prepared as in Example 22 above. Calf thymus DNA (1 mg/mL in TE) is sheared lightly by three passages through a 22 gauge needle. A dilution series of the sheared DNA is prepared in TE and 1 μL of each sample is spotted onto a positively charged nylon filter membrane. The membrane is air dried and the DNA is immobilized by illumination for ~5 minutes with 300 nm light, using a transilluminator. The membrane is incubated for 1 hour in TBS containing 1% BSA. This solution is decanted and replaced with a solution containing 0.5×TBS, 1% BSA and 10–30 μg of a dye-histone conjugate or a dye-bovine serum albumin conjugate. The membrane is incubated in this solution for 3 hours at room temperature, with gentle rotary agitation. The membrane is removed from the solution and epi-illuminated with 254 nm light. A 60 second exposure using POLAROID 667 black-and-white print film and a WRATTEN 15 photographic filter is sufficient to detect 0.1–0.3 μg DNA per spot when the membrane is probed with the histone conjugate. When the membrane is probed with the BSA conjugate, no DNA is detected.

Example 26

Detecting DNA-binding proteins immobilized on filter membranes using dye-DNA conjugates:

DNA is photoaffinity labeled as in Example 21 above. A dilution series of calf thymus histones is prepared in 50 mM Tris-HCl, 138 mM NaCl, 27 mM KCl, pH 8.0 (TBS). A 1 μL aliquot of each dilution is spotted onto a nitrocellulose filter membrane (0.45 μm pore size). The spots are allowed to air dry and the membrane is incubated for 60 minutes at room temperature with TBS containing 0.05% Tween 20 and 1% bovine serum albumin. This solution is decanted and replaced with a solution containing 1–2 μg/mL photoaffinity labeled DNA in 0.5×TBS. The membrane is incubated in this solution for 3 hours at room temperature, with gentle rotary agitation. The membrane is removed from the solution and epi-illuminated with 254 nm light. A 60 second exposure using POLAROID 667 black-and-white print film and a Wratten 15 photographic filter is sufficient to allow 3–10 ng histone per spot to be visualized.

Example 27

Photoaffinity labeling DNA in live cells:

Bovine pulminary aeorta epithelial cells are grown on coverslips, under standard conditions. The cells are stained for 15 minutes with 0.5–5 μM Compound 688 in warm Hanks buffered saline solution (HBSS), then observed with a fluorescence microscope, using a standard fluorescein filter set. Cells are then washed three times with warm HBSS, to remove excess dye, and fixed for 15 minutes in HBSS containing 3.7% formaldehyde; or are photoaffinity labeled by illuminating for 3 minutes using a UV headlamp, then washed three times with HBSS and observed; or are fixed with formaldehyde as above, washed three times with warm HBSS, permeabilized for 1 hour with cold acetone, washed three more times with HBSS, rehydrated for 10 minutes with HBSS, mounted and observed. Stained cells remain brightly fluorescent after photoaffinity labeling as described above, while cells stained with other nucleic acid stains that are not photoaffinity labels do not retain significant fluorescence after having been subsequently fixed and permeabilized.

Example 28

Preparation of dye-labeled microspheres.

Four methods are used to prepare labeled microspheres. In Method A, 1.0 μm uniform amine-derivatized polystyrene microspheres are suspended at ~2% solids in 100 mM bicarbonate buffer pH 8.3 and treated with 2 mg/mL of an amine-reactive dye of the invention such as a succinimidyl ester derivative (for example, Compounds 1029 and 1144)). After 1 hour the microspheres are separated by centrifugation and washed with buffer. In Method B, carboxylate-modified microspheres are suspended in a solution of a protein that has previously been conjugated to a dye of the invention. Alternatively, the microspheres are surface modified by protein, and the protein is then conjugated to a dye of the invention. In either case, excess protein is removed by centrifugation and washing. Microparticles of a size that cannot be centrifuged are separated from protein by dialysis through a semi-permeable membrane with a high MW cutoff or by gel filtration chromatography. In Method C the protein is covalently coupled through its amine residues to the carboxylate groups of the polymer using ethyl 3-(dimethylaminopropyl)carbodiimide (EDAC). In Method D, biotinylated microspheres (Molecular Probes, Inc) are treated with a streptavidin, avidin or anti-biotin conjugate of a dye of the invention and the conjugates are isolated as in Method B. The larger particles can be analyzed for uniformity of staining and brightness using flow cytometry. Magnetic microspheres are particularly useful, as they can be utilized to bind nucleic acids and then may be removed from the sample mixture using magnetic extraction.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula

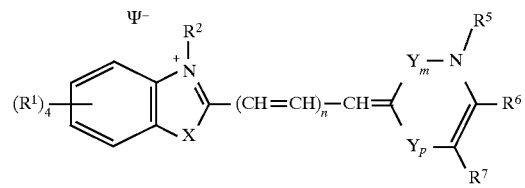

wherein each $R^1$ is independently H; or an alkyl group having from 1–6 carbons; an alkoxy group having from 1–6 carbons; or a trifluoromethyl; or a halogen; or -L-$R_x$;

$R^2$ is an alkyl group having 1–6 carbons; or -L-$R_x$;

X is O, S, Se or $NR^{15}$, where $R^{15}$ is H or an alkyl group having 1–carbons; or X is $CR^{16}R^{17}$ where $R^{16}$ and $R^{17}$, which may be the same or different, are independently alkyl groups having 1–6 carbons;

n=0, 1 or 2;

$\psi^-$ is a compatible counterion;

Y is —$CR^3$=$CR^4$—;

p and m=0 or 1, such that p+m=1;

$R^5$ is an alkyl that is saturated or unsaturated, linear or branched, having 1–6 carbons; or $R^5$ is a cyclic substituent that is an aryl or heteroaryl; or a cycloalkyl; or $R^5$ is a TAIL; or $R^5$ is -L-$R_x$;

$R^4$ is H; or an alkyl that is saturated or unsaturated, linear or branched, having 1–6 carbons; or a halogen; or an aryl or heteroaryl; or a cycloalkyl having 3–10 carbons; or —$OR^8$, —$SR^8$, —($NR^8R^9$); or a TAIL; or -L-$R_x$; where $R^8$ and $R^9$, which can be the same or different, are independently alkyl groups having 1–6 carbons; or 1–2 alicyclic or aromatic rings; or $R^8$ and $R^9$ taken in combination are —($CH_2$)$_2$—V—($CH_2$)$_2$— where V is a single bond, —O—, —$CH_2$—, or —$NR^{10}$—, where $R^{10}$ is H or an alkyl having 1–6 carbons;

$R^3$, $R^6$ and $R^7$ are independently H; or an alkyl that is saturated or unsaturated, linear or branched, having 1–6 carbons; or -L-$R_x$;

or $R^6$ and $R^7$ form a fused aromatic ring such that said compound has the formula

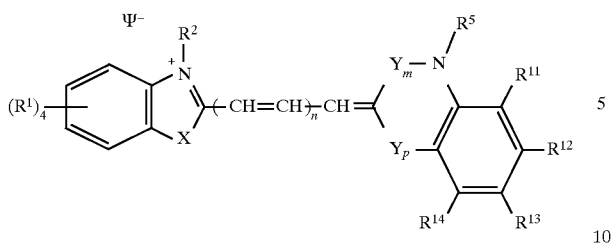

wherein $R^{11}$, $R^{12}$, $R^{13}$, and $R^{14}$, which may be the same or different, are independently H; or an alkyl that is saturated or unsaturated, linear or branched, having 1–6 carbons; or —$OR^8$, —$SR^8$, or —($NR^8R^9$); or a TAIL; or -L-$R_x$;

L is a single covalent bond, or L is a covalent linkage that is linear or branched, cyclic or heterocyclic, saturated or unsaturated, having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

$R_x$ is a reactive group;

TAIL is a heteroatom-containing moiety having the formula LINK-SPACER-CAP; wherein LINK is a single covalent bond, —O—, —S—, or —$NR^{20}$—; where $R^{20}$ is H, a linear or branched alkyl having 1–8 carbons, or $R^{20}$ is -SPACER'-CAP';

SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

CAP and CAP', which may be the same or different, are —O—$R^{21}$, —S—$R^{21}$, —$NR^{21}R^{22}$, or —$N^+R^{21}R^{22}R^{23}\psi^-$; wherein $R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\psi^-$ is a compatible counterion; or CAP and CAP' are independently

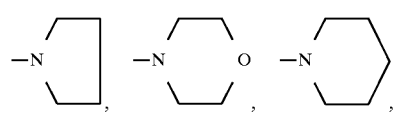

-continued

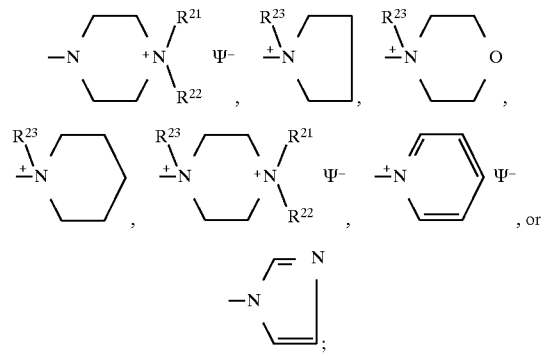

where $R^{21}$, $R^{22}$, $R^{23}$, and $\psi^-$ are as defined previously; such that at least one of $R^1$, $R^2$, $R^3$, $R^4$, $R^5$, $R^6$, $R^7$, $R^{11}$, $R^{12}$, $R^{13}$, and $R^{14}$ is -L-$R_x$; and where more than one of $R^1$ $R^2$, $R^3$, $R^4$, $R^5$, $R^6$, $R^7$, $R^{11}$, $R^{12}$, $R^{13}$, and $R^{14}$ is -L-$R_x$, each -L-$R_x$ is optionally the same or different; provided that when $R^5$ is -L-$R_x$ and m=1, $R^4$ is not hydrogen.

2. A compound, as claimed in claim 1, wherein $R_x$ is a reactive group that is a carboxylic acid, an activated ester of a carboxylic acid, an acyl azide, an acyl halide, an acyl nitrile, an aldehyde, an anhydride, an acrylamide, an alkyl halide, a sulfonate, an aniline, an aryl halide, a thiol, an azide, an aziridine, a boronate, a carbodiimide, a diazoalkane, an epoxide, a glycol, a haloacetamide, a halotriazine, a hydrazine, a hydroxylamine, an imido ester, an isocyanate, an isothiocyanate, a ketone, an aldehyde, a maleimide, a phosphoramidite, a silyl halide, or a sulfonyl halide.

3. A compound, as claimed in claim 1, wherein $R_x$ is an activated ester of a carboxylic acid, an aldehyde, an alkyl halide, a haloacetamide, a halotriazine, a hydrazine, an isothiocyanate, a maleimide, a thiol, or an azide.

4. A compound, as claimed in claim 1, wherein $R^4$ is not hydrogen.

5. A compound, as claimed in claim 1, wherein m=1.

6. A compound, as claimed in claim 1 wherein $R^6$ and $R^7$ form a fused aromatic ring; and at least three of $R^{11}$, $R^{12}$, $R^{13}$ and $R^{14}$ are H.

7. A compound, as claimed in claim 1, wherein $R^5$ is a cyclic substituent that is an aryl or heteroaryl; or a cycloalkyl having 3–10 carbons.

8. A compound, as claimed in claim 1, wherein $R^5$ is -L-$R_x$.

9. A compound, as claimed in claim 8, wherein $R^4$ is -L-$R_x$, and m=1.

10. A compound, as claimed in claim 9, wherein $R^1$ and $R^3$ are H; $R^2$ is methyl or ethyl; X is O or S; $R^5$ is an alkyl having 1–6 carbons, or an aryl or heteroaryl; or $R^5$ is a TAIL; $R^6$ and $R^7$ form a fused aromatic ring; at least three of $R^{11}$, $R^{12}$, $R^{13}$, and $R^{14}$ are H; and n=0 or 1.

11. A compound, as claimed in claim 8, wherein $R^4$ is an alkyl that is saturated or unsaturated, linear or branched having 1–6 carbons; or an aryl or heteroaryl; or a cycloalkyl having 3–10 carbons; or —$OR^8$, —$SR^8$, —($NR^8R^9$); or $R^4$ is a TAIL.

12. A compound, as claimed in claim 1, wherein $R^1$ and $R^3$ are H; $R^2$ is methyl or ethyl; X is O or S; $R^5$ is an alkyl having 1–6 carbons, or an aryl or heteroaryl; or $R^5$ is a TAIL; or $R^5$ is -L-$R_x$; $R^6$ and $R^7$ form a fused aromatic ring; at least three of $R^{11}$, $R^{12}$, $R^{13}$, and $R^{14}$ are H; and n=0 or 1.

13. A compound, as claimed in claim 12, wherein $R^5$ is aryl or heteroaryl.

14. A compound, as claimed in claim 12, wherein one of $R^4$ and $R^5$ is -L-$R_x$.

15. A compound of the formula

[chemical structure]

wherein
- each $R^1$ is independently H; or an alkyl group having from 1–6 carbons; an alkoxy group having from 1–6 carbons; or a trifluoromethyl; or a halogen; or -L-$S_c$;
- $R^2$ is an alkyl group having 1–6 carbons; or -L-$S_c$;
- X is O, S, Se or $NR^{15}$, where $R^{15}$ is H or an alkyl group having 1–6 carbons; or X is $CR^{16}R^{17}$ where $R^{16}$ and $R^{17}$, which may be the same or different, are independently alkyl groups having 1–6 carbons;
- n=0, 1 or 2;
- $\psi^-$ is a compatible counterion;
- Y is —$CR^3$=$CR^4$—;
- p and m=0 or 1, such that p+m=1;
- $R^5$ is an alkyl that is saturated or unsaturated, linear or branched, having 1–6 carbons; or $R^5$ is a cyclic substituent that is an aryl or heteroaryl; or a cycloalkyl; or $R^5$ is a TAIL; or $R^5$ is -L-$S_c$;
- $R^4$ is H; or an alkyl that is saturated or unsaturated, linear or branched, having 1–6 carbons; or a halogen; or an aryl or heteroaryl; or a cycloalkyl having 3–10 carbons; or —$OR^8$, —$SR^8$, —($NR^8R^9$); or a TAIL; or -L-$S_c$; where $R^8$ and $R^9$, which can be the same or different, are independently alkyl groups having 1–6 carbons; or 1–2 alicyclic or aromatic rings; or $R^8$ and $R^9$ taken in combination are —$(CH_2)_2$—V—$(CH_2)_2$— where V is a single bond, —O—, —$CH_2$—, or —$NR^{10}$—, where $R^{10}$ is H or an alkyl having 1–6 carbons;
- $R^3$, $R^6$ and $R^7$ are independently H; or an alkyl that is saturated or unsaturated, linear or branched, having 1–6 carbons; or -L-$S_c$;
- or $R^6$ and $R^7$ form a fused aromatic ring such that said compound has the formula

[chemical structure]

wherein $R^{11}$, $R^{12}$, $R^{13}$, and $R^{14}$, which may be the same or different, are independently H; or an alkyl that is saturated or unsaturated, linear or branched, having 1–6 carbons; or —$OR^8$, —$SR^8$, or —($NR^8R^9$); or a TAIL; or -L-$S_c$;

L is a single covalent bond, or L is a covalent linkage that is linear or branched, cyclic or heterocyclic, saturated or unsaturated, having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

$S_c$ is a conjugated substance;

TAIL is a heteroatom-containing moiety having the formula LINK-SPACER-CAP; wherein
- LINK is a single covalent bond, —O—, —S—, or —$NR^{20}$—; where $R^{20}$ is H, a linear or branched alkyl having 1–8 carbons, or $R^{20}$ is -SPACER'-CAP';
- SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;
- CAP and CAP', which may be the same or different, are —O—$R^{21}$, —S—$R^{21}$, —$NR^{21}R^{22}$, or —$N^+R^{21}R^{22}R^{23}\psi^-$; wherein
  - $R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\psi^-$ is a compatible counterion; or
- CAP and CAP' are independently

[chemical structures of ring groups]

where $R^{21}$, $R^{22}$, $R^{23}$, and $\psi^-$ are as defined previously; such that at least one of $R^1$, $R^2$, $R^3$, $R^4$, $R^5$, $R^6$, $R^7$, $R^{11}$, $R^{12}$, $R^{13}$, and $R^{14}$ is -L-$S_c$; and where more than one of $R^1$, $R^2$, $R^3$, $R^4$, $R^5$, $R^6$, $R^7$, $R^{11}$, $R^{12}$, $R^{13}$, and $R^{14}$ is -L-$S_c$, each -L-$S_c$ is optionally the same or different; provided that when $R^5$ is -L-$S_c$ and m=1, $R^4$ is not hydrogen.

16. A compound, as claimed in claim 15, wherein $S_c$ is a member of a specific binding pair.

17. A compound, as claimed in claim 16, wherein $S_c$ is a drug or a hapten.

18. A compound, as in claim 15, wherein $S_c$ is an amino acid, peptide, protein, polysaccharide, a nucleic acid base, nucleoside, nucleotide or a nucleic acid polymer, lipid, lipophilic polymer, non-biological organic polymer, polymeric microparticle, animal cell, plant cell, bacterium, yeast, or virus.

19. A compound, as claimed in claim 18, wherein $S_c$ is an amino acid, peptide, protein, nucleotide, a nucleic acid polymer, a polysaccharide, or a non-biological organic polymer or polymeric microparticle.

20. A compound, as claimed in claim 19, wherein $S_c$ is a protein, or a nucleic acid polymer.

21. A compound, as claimed in claim 15, wherein $S_c$ is an enzyme, or an enzyme substrate.

22. A compound, as claimed in claim 15, wherein neither $R^1$ nor $R^2$ is -L-$S_c$.

23. A compound, as claimed in claim 15, wherein $R^4$ is not hydrogen.

24. A compound, as claimed in claim 15, wherein m=1.

25. A compound, as claimed in claim 15 wherein $R^6$ and $R^7$ form a fused aromatic ring; and at least three of $R^{11}$, $R^{12}$, $R^{13}$ and $R^{14}$ are H.

26. A compound, as claimed in claim 15 wherein $R^5$ is a cyclic substituent that is an aryl or heteroaryl; or a cycloalkyl having 3–10 carbons.

27. A compound, as claimed in claim 15, wherein $R^5$ is -L-$S_c$.

28. A compound, as claimed in claim 15, wherein $R^4$ is -L-$S_c$ and m=1.

29. A compound, as claimed in claim 15, wherein $R^1$ and $R^3$ are H; $R^2$ is methyl or ethyl; X is O or S; $R^5$ is an alkyl having 1–6 carbons, or an aryl or heteroaryl; or $R^5$ is a TAIL; $R^6$ and $R^7$ form a fused aromatic ring; at least three of $R^{11}$, $R^{12}$, $R^{13}$, and $R^{14}$ are H; and n=0 or 1.

30. A compound, as claimed in claim 15, wherein $R^4$ is an alkyl that is saturated or unsaturated, linear or branched having 1–6 carbons; or an aryl or heteroaryl; or a cycloalkyl having 3–10 carbons; or —$OR^8$, —$SR^8$, —($NR^8R^9$); or $R^4$ is a TAIL.

31. A compound, as claimed in claim 15 wherein $R^1$ and $R^3$ are H; $R^2$ is methyl or ethyl; X is O or S; $R^5$ is an alkyl having 1–6 carbons, or an aryl or heteroaryl; or $R^5$ is a TAIL; $R^6$ and $R^7$ form a fused aromatic ring; at least three of $R^{11}$, $R^{12}$, $R^{13}$, and $R^{14}$ are H; and n=0 or 1.

32. A compound, as claimed in claim 31, wherein $R^5$ is aryl or heteroaryl.

33. A complex comprising a nucleic acid polymer non-covalently bound to a dye of the formula

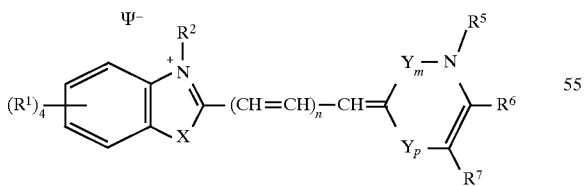

wherein
each $R^1$ is independently H; or an alkyl group having from 1–6 carbons; an alkoxy group having from 1–6 carbons; or a trifluoromethyl; or a halogen; or -L-$R_x$; or -L-$S_c$;

$R^2$ is an alkyl group having 1–6 carbons; or -L-$R_x$; or -L-$S_c$;

X is O, S, Se or $NR^{15}$, where $R^{15}$ is H or an alkyl group having 1–6 carbons; or X is $CR^{16}R^{17}$ where $R^{16}$ and $R^{17}$, which may be the same or different, are independently alkyl groups having 1–6 carbons;

n=0, 1 or 2;

$\psi^-$ is a compatible counterion;

Y is —$CR^3$=$CR^4$—;

p and m=0 or 1, such that p+m=1;

$R^5$ is an alkyl that is saturated or unsaturated, linear or branched, having 1–6 carbons; or $R^5$ is a cyclic substituent that is an aryl or heteroaryl; or a cycloalkyl; or $R^5$ is a TAIL; or $R^5$ is -L-$R_x$; or $R^5$ is -L-$S_c$;

$R^4$ is H; or an alkyl that is saturated or unsaturated, linear or branched, having 1–6 carbons; or a halogen; or an aryl or heteroaryl; or a cycloalkyl having 3–10 carbons; or —$OR^8$, —$SR^8$, —($NR^8R^9$); or a TAIL; or -L-$R_x$; or -L-$S_c$; where $R^8$ and $R^9$, which can be the same or different, are independently alkyl groups having 1–6 carbons; or 1–2 alicyclic or aromatic rings; or $R^8$ and $R^9$ taken in combination are —($CH_2$)$_2$—V—($CH_2$)$_2$— where V is a single bond, —O—, —$CH_2$—, or —$NR^{10}$—, where $R^{10}$ is H or an alkyl having 1–6 carbons;

$R^3$, $R^6$ and $R^7$ are independently H; or an alkyl that is saturated or unsaturated, linear or branched, having 1–6 carbons; or -L-$R_x$; or -L-$S_c$;

or $R^6$ and $R^7$ form a fused aromatic ring such that said compound has the formula

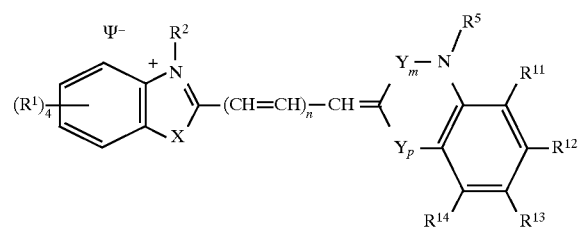

wherein $R^{11}$, $R^{12}$, $R^{13}$, and $R^{14}$, which may be the same or different, are independently H; or an alkyl that is saturated or unsaturated, linear or branched, having 1–6 carbons; or —$OR^8$, —$SR^8$, or —($NR^8R^9$); or a TAIL; or -L-$R_x$; or -L-$S_c$;

each L is a single covalent bond, or L is a covalent linkage that is linear or branched, cyclic or heterocyclic, saturated or unsaturated, having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

$R_x$ is a reactive group;

$S_c$ is a conjugated substance;

TAIL is a heteroatom-containing moiety having the formula LINK-SPACER-CAP; wherein LINK is a single covalent bond, —O—, —S—, or —$NR^{20}$—; where $R^{20}$ is H, a linear or branched alkyl having 1–8 carbons, or $R^{20}$ is -SPACER'-CAP';

SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

CAP and CAP', which may be the same or different, are $-O-R^{21}$, $-S-R^{21}$, $-NR^{21}R^{22}$, or $-N^+R^{21}R^{22}R^{23}\psi^-$; wherein $R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\psi^-$ is a compatible counterion; or CAP and CAP' are independently

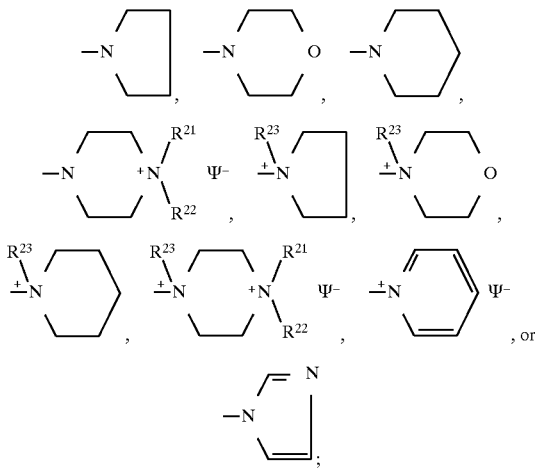

where $R^{21}$, $R^{22}$, $R^{23}$, and $\psi^-$ are as defined previously;

such that at least one of $R^1$, $R^2$, $R^3$, $R^4$, $R^5$, $R^6$, $R^7$, $R^{11}$, $R^{12}$, $R^{13}$, and $R^{14}$ is -L-$R_x$ or -L-$S_c$; and where more than one of $R^1$ $R^2$, $R^3$, $R^4$, $R^5$, $R^6$, $R^7$, $R^{11}$, $R^{12}$, $R^{13}$, and $R^{14}$ is -L-$R_x$ or -L-$S_c$, each -L-$R_x$ and -L-$S_c$ is optionally the same or different; provided that when $R^5$ is -L-$R_x$ or -L-$S_c$ and m=1, $R^4$ is not hydrogen.

34. A complex, as claimed in claim 33, wherein one of $R^1$, $R^2$, $R^3$, $R^4$, $R^5$, $R^6$, $R^7$, $R^{11}$, $R^{12}$, $R^{13}$, and $R^{14}$ is -L-$S_c$, and $S_c$ is a member of a specific binding pair.

35. A complex, as claimed in claim 34, wherein the specific binding pair member is a drug, a hapten, an enzyme, an enzyme substrate, an oligonucleotide, or a peptide.

36. A complex, as claimed in claim 33, wherein $S_c$ is an organic polymer.

37. A complex, as claimed in claim 36, wherein $S_c$ is a polymeric microparticle, or a polymeric membrane.

38. A complex, as claimed in claim 36, wherein $S_c$ is poly(ethylene glycol) or a polysaccharide.

39. A complex, as claimed in claim 33, wherein $R^4$ is not hydrogen, m=1, $R^6$ and $R^7$ form a fused aromatic ring; and at least three of $R^{11}$, $R^{12}$, $R^{13}$ and $R^{14}$ are H.

40. A compound, as claimed in claim 39, wherein $R^4$ is an alkyl that is saturated or unsaturated, linear or branched having 1–6 carbons; or an aryl or heteroaryl; or a cycloalkyl having 3–10 carbons; or $-OR^8$, $-SR^8$, $-(NR^8R^9)$; or $R^4$ is a TAIL.

41. A complex, as claimed in claim 33, wherein $R^5$ is a cyclic substituent that is an aryl or heteroaryl; or a cycloalkyl having 3–10 carbons and $R^4$ is -L-$R_x$ or -L-$S_c$.

42. A complex, as claimed in claim 33, wherein $R^5$ is -L-$R_x$ or -L-$S_c$.

43. A complex, as claimed in claim 33, wherein $R^4$ is -L-$R_x$ or -L-$S_c$.

44. A method of forming a nucleic acid complex, comprising
a) combining a sample that contains or is thought to contain a nucleic acid, with a mixture containing a compound of the formula

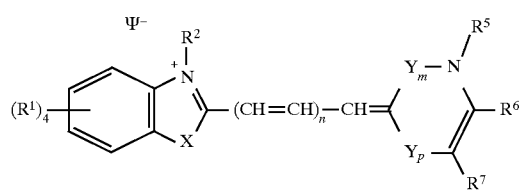

wherein each $R^1$ is independently H; or an alkyl group having from 1–6 carbons; an alkoxy group having from 1–6 carbons; or a trifluoromethyl; or a halogen; or -L-$R_x$; or -L-$S_c$;

$R^2$ is an alkyl group having 1–6 carbons; or -L-$R_x$; or -L-$S_c$;

X is O, S, Se or $NR^{15}$, where $R^{15}$ is H or an alkyl group having 1–6 carbons; or X is $CR^{16}R^{17}$ where $R^{16}$ and $R^{17}$, which may be the same or different, are independently alkyl groups having 1–6 carbons;

n=0, 1 or 2;

$\psi^-$ is a compatible counterion;

Y is $-CR^3=CR^4-$;

p and m=0 or 1, such that p+n=1;

$R^5$ is an alkyl that is saturated or unsaturated, linear or branched, having 1–6 carbons; or $R^5$ is a cyclic substituent that is an aryl or heteroaryl; or a cycloalkyl; or $R^5$ is a TAIL; or $R^5$ is -L-$R_x$; or $R^5$ is -L-$S_c$;

$R^4$ is H; or an alkyl that is saturated or unsaturated, linear or branched, having 1–6 carbons; or a halogen; or an aryl or heteroaryl; or a cycloalkyl having 3–10 carbons; or $-OR^8$, $-SR^8$, $-(NR^8R^9)$; or a TAIL; or -L-$R_x$; or -L-$S_c$; where $R^8$ and $R^9$, which can be the same or different, are independently alkyl groups having 1–6 carbons; or 1–2 alicyclic or aromatic rings; or $R^8$ and $R^9$ taken in combination are $-(CH_2)_2-V-(CH_2)_2-$ where V is a single bond, $-O-$, $-CH_2-$, or $-NR^{10}-$, where $R^{10}$ is H or an alkyl having 1–6 carbons;

$R^3$, $R^6$ and $R^7$ are independently H; or an alkyl that is saturated or unsaturated, linear or branched, having 1–6 carbons; or -L-$R_x$; or -L-$S_c$;

or $R^6$ and $R^7$ form a fused aromatic ring such that said compound has the formula

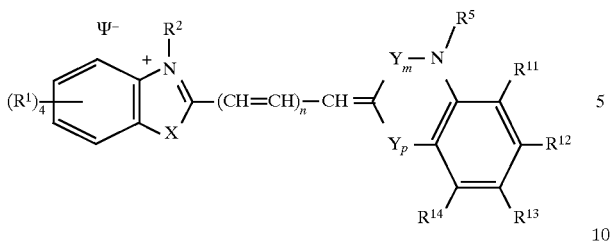

wherein $R^{11}$, $R^{12}$, $R^{13}$, and $R^{14}$, which may be the same or different, are independently H; or an alkyl that is saturated or unsaturated, linear or branched, having 1–6 carbons; or —$OR^8$, —$SR^8$, or —($NR^8R^9$); or a TAIL; or -L-$R_x$; or -L-$S_c$;

each L is a single covalent bond, or L is a covalent linkage that is linear or branched, cyclic or heterocyclic, saturated or unsaturated, having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

$R_x$ is a reactive group;

$S_c$ is a conjugated substance;

TAIL is a heteroatom-containing moiety having the formula LINK-SPACER-CAP; wherein LINK is a single covalent bond, —O—, —S—, or —$NR^{20}$—; where $R^{20}$ is H, a linear or branched alkyl having 1–8 carbons, or $R^{20}$ is -SPACER'-CAP';

SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

CAP and CAP', which may be the same or different, are —O—$R^{21}$, —S—$R^{21}$, —$NR^{21}R^{22}$, or —$N^+R^{21}R^{22}R^{23}\psi^-$; wherein $R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\psi^-$ is a compatible counterion; or CAP and CAP' are independently

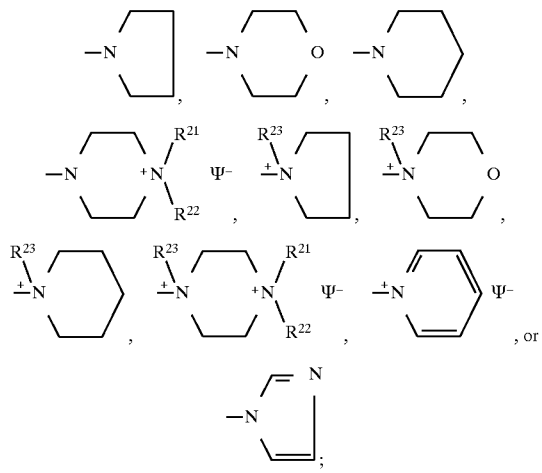

; where $R^{21}$, $R^{22}$, $R^{23}$, and $\psi^-$ are as defined previously;

such that at least one of $R^1$, $R^2$, $R^3$, $R^4$, $R^5$, $R^6$, $R^7$, $R^{11}$, $R^{12}$, $R^{13}$, and $R^{14}$ is -L-$R_x$ or -L-$S_c$; and where more than one of $R^1$ $R^2$, $R^3$, $R^4$, $R^5$, $R^6$, $R^7$, $R^{11}$, $R^{12}$, $R^{13}$, and $R^{14}$ is -L-$R_x$ or -L-$S_c$, each -L-$R_x$ and -L-$S_c$ is optionally the same or different; provided that when $R^5$ is -L-$R_x$ or -L-$S_c$ and m=1, $R^4$ is not hydrogen; and b) incubating the sample and mixture for a time sufficient for the compound to associate non-covalently with the nucleic acid in the sample to form one or more nucleic acid complexes.

45. A method, as claimed in claim 44, wherein said nucleic acid complex exhibits a detectable optical response.

46. A method, as claimed in claim 45, wherein the detectable optical response is a fluorescence response.

47. A method, as claimed in claim 45, wherein one of $R^1$, $R^2$, $R^3$, $R^4$, $R^5$, $R^6$, $R^7$, $R^{11}$, $R^{12}$, $R^{13}$, and $R^{14}$ is -L-$S_c$.

48. A method, as claimed in claim 47, further comprising separating the nucleic acid complex from the sample.

49. A method, as claimed in claim 47, wherein $S_c$ is an organic polymer.

50. A method, as claimed in claim 49, wherein $S_c$ is poly(ethylene glycol) or a polysaccharide.

51. A method, as claimed in claim 47, wherein $S_c$ is a polymeric microparticle, or a polymeric membrane.

52. A method, as claimed in claim 51, wherein the polymeric microparticle is a magnetic microparticle and, further comprising separating the nucleic acid complex from the sample by removing the magnetic microparticle from the sample.

53. A method, as claimed in claim 47, wherein $S_c$ is a first member of a specific binding pair having a first and second member.

54. A method, as claimed in claim 53, wherein the formation of said complex indicates the location of the second member of the specific binding pair in the sample.

55. A method, as claimed in claim 53, wherein the first member is a drug, a hapten, an enzyme substrate, a nucleic acid polymer, a peptide, or a protein.

56. A method, as claimed in claim 53, wherein the first member is a biotin, a digoxigenin, an avidin, a streptavidin, or an antibody.

57. A method, as claimed in claim 54, wherein the sample comprises one or more cells, bacteria, virus, yeast cells, or a polymeric membrane or polymeric microparticles.

58. A method, as claimed in claim 44, wherein $R^4$ is not hydrogen, m=1, $R^6$ and $R^7$ form a fused aromatic ring; and at least three of $R^{11}$, $R^{12}$, $R^{13}$ and $R^{14}$ are H.

59. A method, as claimed in claim 44, wherein $R^4$ is an alkyl that is saturated or unsaturated, linear or branched having 1–6 carbons; or an aryl or heteroaryl; or a cycloalkyl having 3–10 carbons; or $—OR^8$, $—SR^8$, $—(NR^8R^9)$; or $R^4$ is a TAIL.

60. A method, as claimed in claim 44, wherein $R^5$ is a cyclic substituent that is an aryl or heteroaryl; or a cycloalkyl having 3–10 carbons and $R^4$ is $-L-R_x$ or $-L-S_c$.

61. A method, as claimed in claim 44, wherein $R^5$ is $-L-R_x$ or $-L-S_c$.

62. A method, as claimed in claim 44, wherein $R^4$ is $-L-R_x$ or $-L-S_c$.

63. A compound of the formula

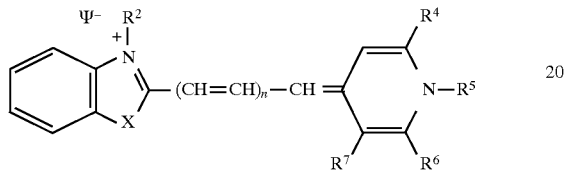

wherein X is O or S;

$R^2$ is an alkyl group having 1–6 carbons;

n=0, 1 or 2;

$\psi^-$ is a compatible counterion;

$R^4$ is an aryl or heteroaryl that is optionally substituted by halogen, alkyl, perfluoroalkyl, amino, alkylamino, dialkylamino, alkoxy or carboxyalkyl, each alkyl group having 1–6 carbons; or is substituted by TAIL; or is substituted by $-L-R_x$;

$R^5$ is an alkyl that is saturated or unsaturated, linear or branched, having 1–6 carbons; an aryl or heteroaryl; or $R^5$ is a TAIL; or $R^5$ is $-L-R_x$;

$R^3$, $R^6$ and $R^7$ are independently H; or an alkyl that is saturated or unsaturated, linear or branched, having 1–6 carbons; or $R^6$ and $R^7$ form a fused aromatic ring such that said compound has the formula

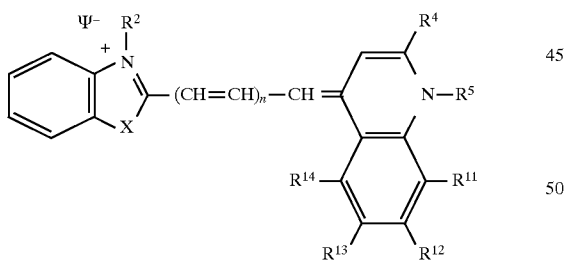

wherein $R^{11}$, $R^{12}$, $R^{13}$, and $R^{14}$, which may be the same or different, are independently H; or an alkyl that is saturated or unsaturated, linear or branched, having 1–6 carbons; or an alkoxy having 1–6 carbons; or $—OR^8$, $—SR^8$, or $—(NR^8R^9)$ where $R^8$ and $R^9$, which can be the same or different, are independently alkyl groups having 1–6 carbons; or 1–2 alicyclic or aromatic rings; or $R^8$ and $R^9$ taken in combination are $—(CH_2)_2—V—(CH_2)_2—$ where V is a single bond, $—O—$, $—CH_2—$, or $—NR^{10}—$, where $R^{10}$ is H or an alkyl having 1–6 carbons; or a TAIL;

L is a single covalent bond, or L is a covalent linkage that is linear or branched, cyclic or heterocyclic, saturated or unsaturated, having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

$R_x$ is a reactive group;

TAIL is a heteroatom-containing moiety having the formula LINK-SPACER-CAP; wherein LINK is a single covalent bond, $—O—$, $—S—$, or $—NR^{20}—$; where $R^{20}$ is H, a linear or branched alkyl having 1–8 carbons, or $R^{20}$ is -SPACER'-CAP';

SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

CAP and CAP', which may be the same or different, are $—O—R^{21}$, $—S—R^{21}$, $—NR^{21}R^{22}$, or $—N^+R^{21}R^{22}R^{23}\psi^-$; wherein $R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N, S; where $\psi^-$ is a compatible counterion; or CAP and CAP' are independently

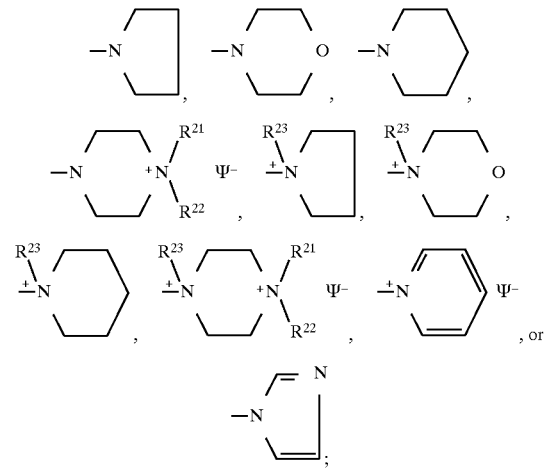

where $R^{21}$, $R^{22}$, $R^{23}$, and $\psi^-$ are as defined previously.

64. A compound, as claimed in claim 63, wherein $R^4$ is a naphthyl, a phenyl, a thienyl, a benzothiazolyl, a furanyl, an oxazolyl, a benzoxazolyl, or a pyridinyl that is optionally substituted by halogen, alkyl, perfluoroalkyl, amino, alkylamino, dialkylamino, alkoxy or carboxyalkyl, each alkyl group having 1–6 carbons; or by TAIL; or -L-$R_x$.

65. A compound, as claimed in claim 64, wherein $R^4$ is substituted by TAIL or -L-$R_x$.

66. A compound, as claimed in claim 65, wherein $R^4$ is substituted by TAIL having the formula LINK-SPACER-CAP;

wherein LINK is a single covalent bond, —O—, —S—, or —$NR^{20}$—; where $R^{20}$ is H, a linear or branched alkyl having 1–8 carbons, or $R^{20}$ is -SPACER'-CAP';

SPACER and SPACER' independently have the formula —$(CH_2)_k$—, where k=1–8,

CAP and CAP', which may be the same or different, are —$NR^{21}R^{22}$ or —$N^+R^{21}R^{22}R^{23}\psi^-$;

where $R^{21}$, $R^{22}$, and $R^{23}$ are independently methyl or ethyl.

67. A compound, as claimed in claim 64, wherein $R^5$ is an alkyl having 1–6 carbons.

68. A compound of the formula

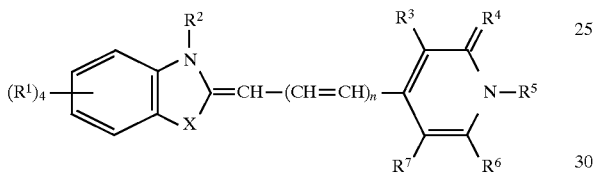

or of the formula

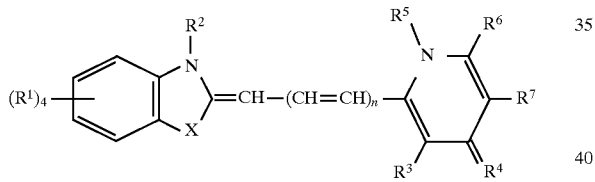

wherein each $R^1$ is independently H; or an alkyl group having from 1–6 carbons; an alkoxy group having from 1–6 carbons; or a trifluoromethyl; or a halogen; or -L-$R_x$;

$R^2$ is an alkyl group having 1–6 carbons; or -L-$R_x$;

X is O, S, Se or $NR^{15}$, where $R^{15}$ is H or an alkyl group having 1–6 carbons; or X is $CR^{16}R^{17}$ where $R^{16}$ and $R^{17}$, which may be the same or different, are independently alkyl groups having 1–6 carbons;

n=0, 1 or 2;

$R^5$ is an alkyl that is saturated or unsaturated, linear or branched, having 1–6 carbons; or $R^5$ is a cyclic substituent that is an aryl or heteroaryl; or a cycloalkyl; or $R^5$ is a TAIL; or $R^5$ is -L-$R_x$;

$R^4$ is $NR^{19}$; where $R^{19}$ is an alkyl group having 1–6 carbons; or an alicyclic or aromatic ring; or $R^{19}$ is -SPACER-CAP; or $R^{19}$ is -L-$R_x$;

$R^3$, $R^6$ and $R^7$ are independently H; or an alkyl that is saturated or unsaturated, linear or branched, having 1–6 carbons; or -L-$R_x$;

or $R^6$ and $R^7$ form a fused aromatic ring such that said compound has the formula

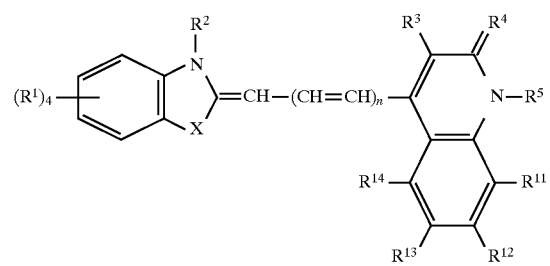

or the formula

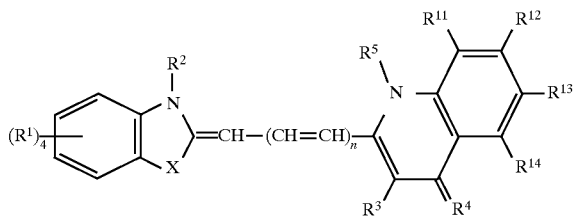

wherein $R^{11}$, $R^{12}$, $R^{13}$, and $R^{14}$, which may be the same or different, are independently H; or an alkyl that is saturated or unsaturated, linear or branched, having 1–6 carbons; or —$OR^8$, —$SR^8$, or —$(NR^8R^9)$, where $R^8$ and $R^9$, which can be the same or different, are independently alkyl groups having 1–6 carbons; or 1–2 alicyclic or aromatic rings; or $R^8$ and $R^9$ taken in combination are —$(CH_2)_2$—V—$(CH_2)_2$— where V is a single bond, —O—, —$CH_2$—, or —$NR^{10}$—, where $R^{10}$ is H or an alkyl having 1–6 carbons; or a TAIL; or -L-$R_x$;

L is a single covalent bond, or L is a covalent linkage that is linear or branched, cyclic or heterocyclic, saturated or unsaturated, having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

$R_x$ is a reactive group;

TAIL is a heteroatom-containing moiety having the formula LINK-SPACER-CAP; wherein LINK is a single covalent bond, —O—, —S—, or —$NR^{20}$—; where $R^{20}$ is H, a linear or branched alkyl having 1–8 carbons, or $R^{20}$ is -SPACER'-CAP';

SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon—carbon bonds; or phosphorus-oxygen, phosphorus-sulfur bonds, nitrogen—nitrogen or nitrogen-oxygen bonds; or aromatic or heteroaromatic bonds;

CAP and CAP', which may be the same or different, are —O—$R^{21}$, —S—$R^{21}$, —$NR^{21}R^{22}$, or —$N^+R^{21}R^{22}R^{23}\psi^-$; wherein $R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\psi^-$ is a compatible counterion; or CAP and CAP' are independently

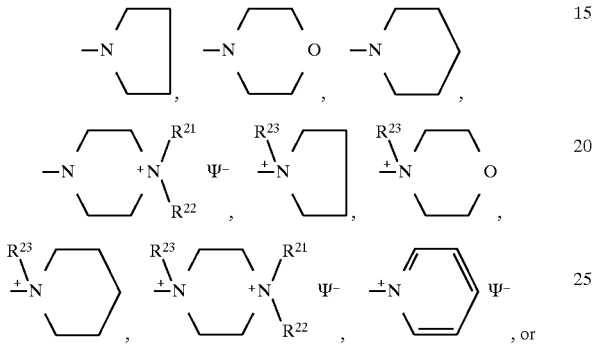

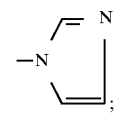

where $R^{21}$, $R^{22}$, $R^{23}$, and $\psi^-$ are as defined previously.

69. A compound, as claimed in claim 68, wherein $R^5$ is aryl or heteroaryl; X is O or S; n is 0 or 1; and $R^6$ and $R^7$ are H; or taken in combination, form a fused aromatic ring.

70. A compound, as claimed in claim 69, wherein $R^5$ is phenyl; and $R^{19}$ is -SPACER-CAP;

wherein SPACER and has the formula —$(CH_2)_k$—, where k=1–8;

CAP is —$NR^{21}R^{22}$ or —$N^+R^{21}R^{22}R^{23}$ $\psi^-$; where $R^{21}$, $R^{22}$, and $R^{23}$ are independently methyl or ethyl, or CAP is

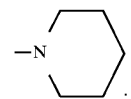

* * * * *

UNITED STATES PATENT AND TRADEMARK OFFICE
CERTIFICATE OF CORRECTION

PATENT NO. : 5,863,753
DATED : January 26, 1999
INVENTOR(S) : Haugland et al.

It is certified that error appears in the above-identified patent and that said Letters Patent is hereby corrected as shown below:

Column 10,
Line 42, "used to form an anhydride" should read -- used to form activated aryl esters; or a carboxylic acid activated by carbodiimide to form an anhydride --.

Column 17,
Line 46, "n1" should read -- n=1 --.

Column 22,
Lines 56 and 58, "TEF" and "TBF", respectively should read -- THF --.

Column 26,
Line 6, "dihydro-3-thiazol-2-yl)methylidene)-1-" should read -- dihydro-3-methyl-(benzo-1,3-thiazol-2-yl)methylidene)-1- --.

Column 32,
Line 39, "1-carbons" should read -- 1-6 carbons --.

Signed and Sealed this

Seventeenth Day of September, 2002

Attest:

JAMES E. ROGAN
Attesting Officer
Director of the United States Patent and Trademark Office